(12) United States Patent
Qiu et al.

(10) Patent No.: US 9,412,951 B2
(45) Date of Patent: Aug. 9, 2016

(54) ORGANIC MATERIALS AND ORGANIC ELECTROLUMINESCENT APPARATUSES USING THE SAME

(75) Inventors: Yong Qiu, Beijing (CN); Yinkui Li, Beijing (CN); Jing Xie, Beijing (CN)

(73) Assignees: BEIJING VISIONOX TECHNOLOGY CO., LTD. (CN); KUNSHAN VISIONOX DISPLAY CO., LTD. (CN); TSINGHUA UNIVERSITY (CN)

(*) Notice: Subject to any disclaimer, the term of this patent is extended or adjusted under 35 U.S.C. 154(b) by 1116 days.

(21) Appl. No.: 13/497,131

(22) PCT Filed: Dec. 30, 2009

(86) PCT No.: PCT/CN2009/076276
§ 371 (c)(1),
(2), (4) Date: Dec. 18, 2012

(87) PCT Pub. No.: WO2011/057461
PCT Pub. Date: May 19, 2011

(65) Prior Publication Data
US 2013/0087771 A1    Apr. 11, 2013

(30) Foreign Application Priority Data

Nov. 13, 2009  (CN) .......................... 2009 1 0234760
Nov. 19, 2009  (CN) .......................... 2009 1 0234478

(51) Int. Cl.
| | |
|---|---|
| H01L 51/54 | (2006.01) |
| C07D 401/14 | (2006.01) |
| C07D 401/10 | (2006.01) |
| H01L 51/00 | (2006.01) |
| C07D 213/53 | (2006.01) |
| C09K 11/06 | (2006.01) |
| H05B 33/14 | (2006.01) |
| H01L 51/50 | (2006.01) |

(52) U.S. Cl.
CPC .......... H01L 51/0052 (2013.01); C07D 213/53 (2013.01); C09K 11/06 (2013.01); H01L 51/0067 (2013.01); H05B 33/14 (2013.01); C09K 2211/1011 (2013.01); C09K 2211/1029 (2013.01); H01L 51/5048 (2013.01)

(58) Field of Classification Search
CPC ........... C09K 2211/1029; C09K 11/06; C09K 2211/1011; H01L 51/0052; H01L 51/5048; H01L 51/0067; H05B 33/14; C07D 213/53
See application file for complete search history.

(56) References Cited

U.S. PATENT DOCUMENTS

| | | | |
|---|---|---|---|
| 6,300,997 B1 | 10/2001 | Saito et al. | |
| 6,545,424 B2 | 4/2003 | Ozawa | |
| 6,847,343 B2 | 1/2005 | Anzai | |
| 7,978,297 B2 | 7/2011 | Kimura et al. | |
| 2004/0150765 A1 | 8/2004 | Ueda et al. | |
| 2005/0116658 A1 | 6/2005 | Kato | |
| 2006/0017373 A1 | 1/2006 | Lee | |
| 2006/0232197 A1 | 10/2006 | Lee | |
| 2006/0243968 A1 | 11/2006 | Chang Chien et al. | |
| 2007/0001682 A1 | 1/2007 | Habitz et al. | |
| 2007/0046189 A1* | 3/2007 | Hatwar et al. | 313/506 |
| 2007/0048545 A1* | 3/2007 | Hatwar et al. | 428/690 |
| 2007/0051958 A1 | 3/2007 | Yamazaki et al. | |
| 2007/0165176 A1 | 7/2007 | Yang et al. | |
| 2007/0262318 A1 | 11/2007 | Shoji et al. | |
| 2008/0111473 A1* | 5/2008 | Kawamura et al. | 313/504 |
| 2008/0152950 A1* | 6/2008 | Je et al. | 428/704 |
| 2008/0284325 A1 | 11/2008 | Noh et al. | |
| 2009/0102364 A1 | 4/2009 | Suh et al. | |
| 2010/0096982 A1* | 4/2010 | Eum et al. | 313/504 |
| 2010/0140603 A1 | 6/2010 | Jeong et al. | |
| 2012/0092017 A1 | 4/2012 | Qiu et al. | |

FOREIGN PATENT DOCUMENTS

| | | |
|---|---|---|
| CN | 1362464 | 8/2002 |
| CN | 1435893 | 8/2003 |
| CN | 1512826 | 7/2004 |
| CN | 1527046 | 9/2004 |
| CN | 1871711 | 11/2006 |

(Continued)

OTHER PUBLICATIONS

Machine translation for CN 101412907 A (publication date: Apr. 2009).*
International Search Report prepared by the the State Intellectual Property Office, the P.R. China, on Sep. 2, 2010, for International Application No. PCT/CN2009/076276.
Pope et al. "Electroluminescence in Organic Crystals"; Chem. Phys., vol. 38, pp. 2042-2043, 1963.
Tang et al. "Organic electroluminescent diodes"; Appl. Phys. Lett. 51(12), p. 913, Sep. 21, 1987.
Burroughes et al. "Light-emitting diodes based on conjugated polymers"; Nature, vol. 347, p. 539, Oct. 11, 1990.
Huang et al. "Low-Work-Function Surface Formed by Solution-Processed and Thermally Deposited Nanoscale Layers of Cesium Carbonate"; Adv. Funct. Mater. 2007, 17, 1966-1973.
Yang et al. "Conjugated Oligoelectrolyte Electron Transport/Injection Layers for Organic Optoelectronic Devices"; J.Am.Chem.Soc. 2008, 130, 3282-3283.

(Continued)

*Primary Examiner* — Dawn Garrett
(74) *Attorney, Agent, or Firm* — Sheridan Ross P.C.

(57) ABSTRACT

Organic materials and organic electroluminescent apparatuses using the same are provided. The structural general formula of the materials is shown below, wherein Ar is selected from residues of C6-C30 fused-ring aromatic hydrocarbons, $Ar_1$ and $Ar_2$ are each independently selected from the group consisting of hydrogen, C6-C24 aryl, and C6-C24 heterocyclic aryl, and n is an integer selected from 2 and 3. The present organic materials can be used as electron transport layers in the organic electroluminescent apparatuses.

(1)

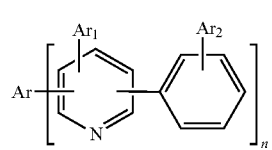

26 Claims, 2 Drawing Sheets

(56) References Cited

FOREIGN PATENT DOCUMENTS

| | | |
|---|---|---|
| CN | 1889800 | 1/2007 |
| CN | 101077971 | 11/2007 |
| CN | 101087759 A | 12/2007 |
| CN | 101188247 | 5/2008 |
| CN | 101221971 | 7/2008 |
| CN | 101305071 A | 11/2008 |
| CN | 101308749 | 11/2008 |
| CN | 101364636 A | 2/2009 |
| CN | 101407493 A | 4/2009 |
| CN | 101412907 A | 4/2009 |
| CN | 101452997 A | 6/2009 |
| CN | 200910234478.X | 11/2009 |
| CN | 200910234760.8 | 11/2009 |
| EP | 1850391 | 10/2007 |
| EP | 2112214 | 10/2009 |
| EP | 2141214 | 1/2010 |
| EP | 2161319 | 3/2010 |
| JP | H07-159483 | 6/1995 |
| JP | 2000-134411 | 5/2000 |
| JP | 2003-066870 | 3/2003 |
| JP | 2004-070137 | 3/2004 |
| JP | 2005-241988 | 9/2005 |
| JP | 2006-173550 | 6/2006 |
| JP | 2006-176448 | 7/2006 |
| JP | 2007-147949 | 6/2007 |
| JP | 2007-298938 | 11/2007 |
| JP | 2008-162921 | 7/2008 |
| JP | 2008-169197 | 7/2008 |
| JP | 2009-173642 A | 8/2008 |
| JP | 2009-266927 | 11/2009 |
| KR | 1997-0008537 | 2/1997 |
| KR | 2006-0029086 | 4/2006 |
| KR | 2006-0113552 | 11/2006 |
| KR | 2006-0120328 | 11/2006 |
| KR | 2009-0029111 | 3/2009 |
| KR | 10-2009-0086015 | 8/2009 |
| WO | WO2009000835 A1 | 1/2009 |
| WO | WO 2009008351 | 1/2009 |
| WO | WO 2009/054253 | 4/2009 |
| WO | WO 2009/097084 | 8/2009 |
| WO | WO 2009/136596 | 11/2009 |

OTHER PUBLICATIONS

Wu et al. "High-efficiency electron injection cathode of Au for polymer light-emitting devices"; Organic Electronics, 2005, 6, 118-128.

Office Action dated Sep. 9, 2011, issued by the the State Intellectual Property Office of the People's Republic of China (SIPO) for priority application CN200910234478.X.

Office Action dated Oct. 14, 2011, issued by the the State Intellectual Property Office of the People's Republic of China (SIPO) for priority application CN200910234760.8.

International Search Report prepared by The State Intellectual Property Office, The People's Republic of China, on Apr. 8, 2010, for International Application No. PCT/CN2009/076257.

International Preliminary Report on Patentability for International (PCT) Patent Application No. PCT/CN2009/076257, mailed Dec. 15, 2011.

Extended European Search Report for European Patent Application No. 09845455.6 dated Sep. 17, 2013, 7 pages.

Official Action (with English translation) for Korean Patent Application No. 10-2011-7025657 dated Nov. 25, 2013, 4 pages.

Official Action for U.S. Appl. No. 13/375,688 mailed Nov. 7, 2013, 13 pages.

International Preliminary Report on Patentability for International (PCT) Patent Application No. PCT/CN2009/076276, dated May 15, 2012, 6 pages.

Notice of Allowance for U.S. Appl. No. 13/375,688 mailed May 28, 2014, 10 pages.

Extended European Search Report for European Patent Application No. 09851216.3 dated May 14, 2013, 9 pages.

Je et al, "Preparation of anthracene compounds as n-type organic semiconductor materials for organicelectroluminescent device," 2009, CAPlus Accession No. 2009:364648, 2 pages. (Abstract only).

Oshiyama et al., "Organicelectroluminescent device, display device and illuminating device," 2009, CAPlus Accession No. 2009:519356, 2 pages. (Abstract only).

Oshiyama et al., "Organicelectroluminescent devices for display and light sources and material for the same," 2009, CAPlus Accession No. 2009:1401952, 2 pages. (Abstract only).

Takashima, et al., "Benzothiadiazoles, organicelectroluminescent materials containing them, and blue-emitting organic electroluminescent devices using them," 2008, CAPlus Accession No. 2008:856996, 2 pages. (Abstract only).

Yamamoto et al, "Organicelectroluminescent element," 2009, CAPlus Accession No. 2009:1394448, 2 pages. (Abstract only).

Official Action (with English translation) for Korean Patent Application No. 10-2012-7004954 dated Aug. 16, 2013, 14 pages.

\* cited by examiner

ORGANIC MATERIALS AND ORGANIC ELECTROLUMINESCENT APPARATUSES USING THE SAME

CROSS REFERENCE TO RELATED APPLICATIONS

This application is a national stage application under 35 U.S.C. 371 of PCT Application No. PCT/CN2009/076276 having an international filing date of 30 Dec. 2009, which designated the United States, which PCT application claimed the benefit of Chinese Patent Application No. 200910234760.8 filed 13 Nov. 2009, and Chinese Patent Application No. 200910234478.X filed 19 Nov. 2009, the entire disclosure of each of which is incorporated herein by reference.

FIELD OF THE INVENTION

The present invention relates to a novel organic material and an organic electroluminescent apparatus using the novel organic material, and belongs to the technical field of organic electroluminescent display.

BACKGROUND OF THE INVENTION

Currently, the requirement on performance of a panel display becomes higher due to development of multimedia technique and coming of information society. Organic electroluminescent display has a series of advantages such as autonomous luminescence, direct current driving at a low voltage, full solidification, wide view angle and being colorful. Its response speed is 1,000 times higher than LCD, while its manufacturing cost is lower than LCD having equal resolution. Thus, the organic electroluminescent display has broad prospects.

Research on organic electroluminescent display (also called organic light emitting diode, OLED) starts in 1960's. Electroluminescent phenomenon of single crystal of anthracene is firstly reported by Pope et al. (Pope M., Kallmann H. P. and Magnante R. J., Chem. Phys., 1963, 38, 2042), which preludes organic solid electroluminescence. In 1987, on the basis of summarizing previous researchers' work, the researcher C. W. Tang et al. (C. W. Tang, S. A. Vanslyke, Appl. Phys. Lett., 1987, 51, 913) in Kodak Company, U.S. proposes a design concept of structure of double layer and respectively selects triarylamine compounds and 8-hydroxyquinolinato aluminum complex ($Alq_3$) having a good film-forming property for a hole transport layer and a luminescent layer (also acting as an electron transport layer), leading to an organic electroluminescent apparatus having high quantum efficiency (>1%), high efficiency (1.5 1 m/W), high luminance (>1000 $cd/m^2$) and low driving voltage (<10V). In 1990, Burroughes et al. Nature, 1990, 347, 539-41) in Cavendish laboratory of University of Cambridge prepares a polymer electroluminescent apparatus by using polyphenylene vinylene (PPV) as a material for luminescent layer, and sets up another new field of light emitting apparatus, polymer thin film electroluminescent apparatus. These two significant progresses make the organic electroluminescent apparatus have potential to be a new generation of panel display.

The organic electroluminescent apparatus is composed of two opposite electrodes and an organic medium between the electrodes, the organic medium including a hole injection layer, a hole transport layer, a luminescent layer, an electron transport layer, a charge blocking layer and the like. It is generally believed that holes are often more than electrons in the OLED apparatus, causing imbalance of two carriers at interface of recombination and reducing luminance and efficiency of the apparatus. Meanwhile, redundant holes are easily transported into the electron transport layer and even a cathode, which accelerate aging of the apparatus and shorten life of OLED. Therefore, enhancing the injection and transport of electron become a subject being concerned and investigated extensively in the field. In addition to the cathode being highly efficient and stable, a hole blocking layer, the electron transport layer and the electron injection are disposed between the luminescent layer and the cathode, respectively performing functions of blocking holes to restrict excitons in the emissive region, transport electrons, and injecting electrons.

An electron transport material conventionally used in the organic electroluminescent apparatus is $Alq_3$, but it has a lower electron mobility (at about $10^{-6}$ $cm^2/Vs$). In order to enhance the electron transport property of the organic electroluminescent apparatus, much exploratory development has been made. Huang et al. employs nanometer cesium carbonate as an electron transport and injection material in the organic electroluminescent apparatus, thereby increasing luminous efficiency of the apparatus (Advanced Functional Materials, 2007, 17, 1966-1973). It is reported by LG Chemical Co. Ltd. that when benzimidazole, benzothiazole or benzoxazole compounds are used as an electron transport material in the organic electroluminescent apparatus, electron transport property of the apparatus is improved and turn-on voltage is reduced. (Chinese Patent Application No. 200680041587.4 with Publication Number CN 101305071A). When ammonium salt of derivative of terfluorene (abbreviated FFF-B1m4) synthesized by Cao Yong et al. (J. Am. Chem. Soc., 2008, 130(11), 3282-3283) is used a material for an electron injection layer, electron injection and transport of the apparatus are significantly improved, and electroluminescent efficiency is increased. Yang et al. also uses gold which is stable to air and various chemical corrosion as a cathode material of high efficient electron injection type, which improve electron injection ability of the organic electroluminescent apparatus (Organic Electronics, 2005, 6, 118-128). It is very important to develop stable and highly efficient electron transport material and/or electron injection material, thereby reducing turn-on voltage, improving efficiency of the apparatus, and increasing life of the apparatus.

A desirable electron transport material should have following characteristics: reversible electrochemical reduction reaction, suitable HOMO and LUMO levels, high electron mobility, good film-forming ability, high Tg, and preferably blocking holes. In terms of structure of compound, it is required that molecular configuration is close to plane, thereby enhancing π-π interaction among molecules when the molecules are stacked, while it is required that the structure of the molecule is not completely planar, thereby preventing the film-forming property from being affected by crystallization of the molecule; it is required that the molecule contains a structural unit lack of electron, thereby possessing good electron accepting ability; and the molecular weight is high enough to ensure high Tg and thus good thermal stability, while the molecular weigh can not be too high in order to facilitate film-forming by vacuum deposition.

SUMMARY OF THE INVENTION

A compound containing a pyridyl group is a typical system lack of electron and has good electron accepting ability. Planar regularity of fused-ring aromatic compounds is better. Larger the fused-ring system is, better the planarity is, which is more beneficial for stacking π-π orbits of molecules and forming electron channels. However, if the fused-ring system is too large, the molecules are prone to form crystals instead of forming a film. Thus, in the present invention, a benzene ring is introduced to be connected with the pyridyl group on the basis of the fused-ring system to sterically generate distortion to a certain degree and enhance its film-forming property. In view of its practicability and whether vacuum deposition is easy, the electron transport material of the present invention generally has a molecular weight of less than 800.

Based on the above consideration, the present invention develops a novel organic material having good thermal stability and high electron mobility, which can be used as a material having stronger electron transport ability in the organic electroluminescent apparatus.

The present invention provides an organic material represented by following structural general formula:

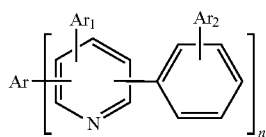

wherein Ar is selected from residues of C6-C30 fused-ring aromatic hydrocarbons, $Ar_1$ and $Ar_e$ are each independently selected from the group consisting of hydrogen, C6-C24 aryl, and C6-C24 heterocyclic aryl, and n is an integer selected from 2 and 3.

The present invention also provides use of the organic material in an electron transport material in an organic electroluminescent apparatus.

The present invention also provides an organic electroluminescent apparatus comprising a pair of electrodes and an organic luminescent medium disposed between the pair of electrodes, the organic luminescent medium comprising the organic material.

DETAILED DESCRIPTION

Figure 1:
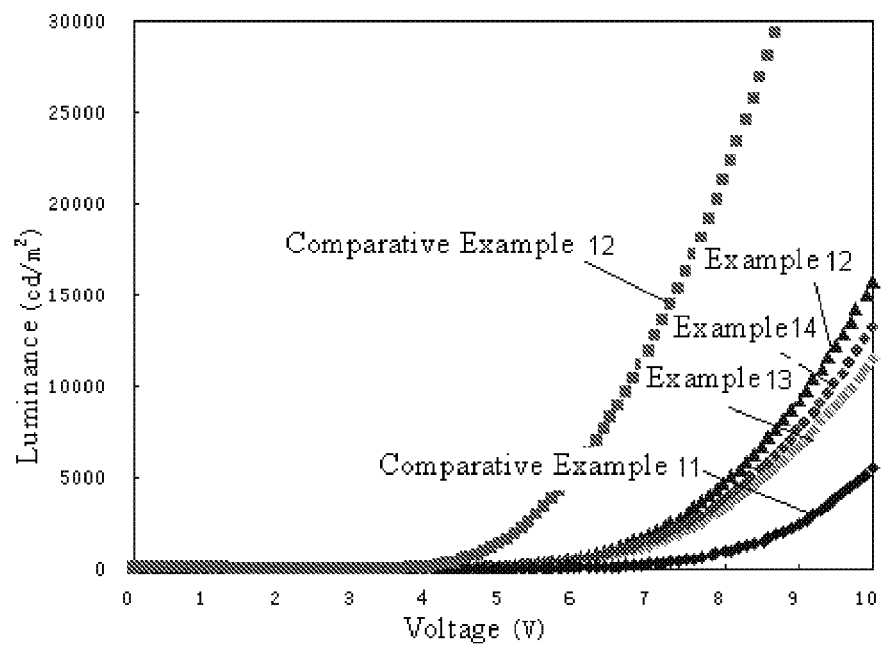
FIG. 1 is a graph illustrating luminance with respect to voltage of light emitting apparatuses of Examples 12 to 14 and Comparative Examples 11 to 12.
Figure 2:
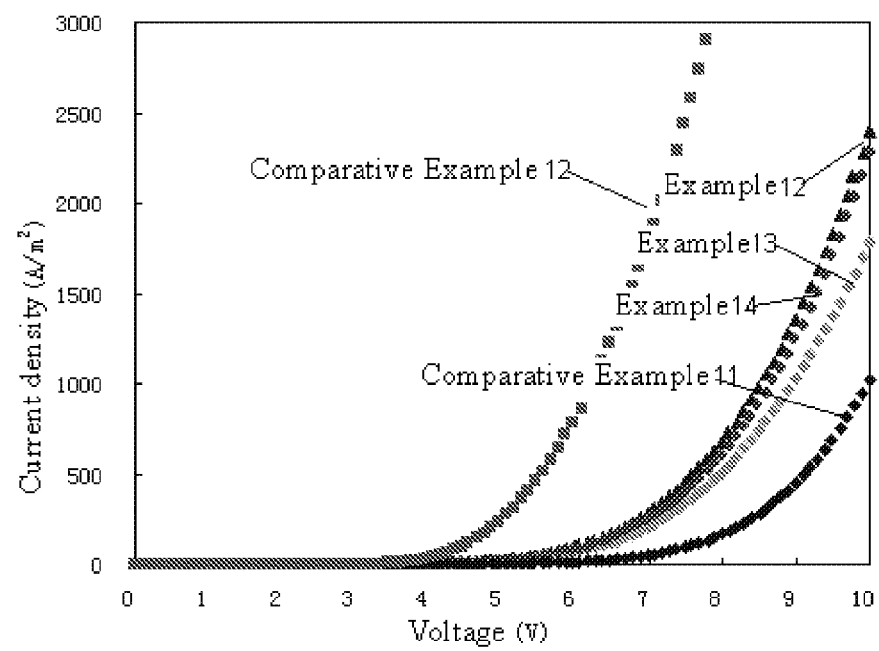
FIG. 2 is a graph illustrating current density with respect to voltage of light emitting apparatuses of Examples 12 to 14 and Comparative Examples 11 to 12.
Figure 3:
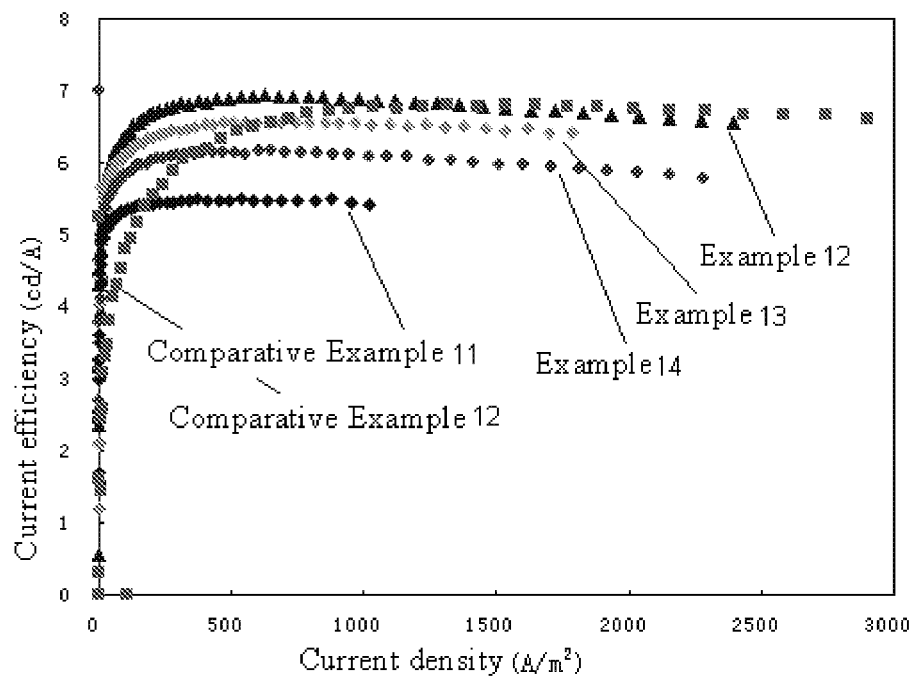
FIG. 3 is a graph illustrating current efficiency with respect to current density of light emitting apparatuses of Examples 12 to 14 and Comparative Examples 11 to 12.
Figure 4:
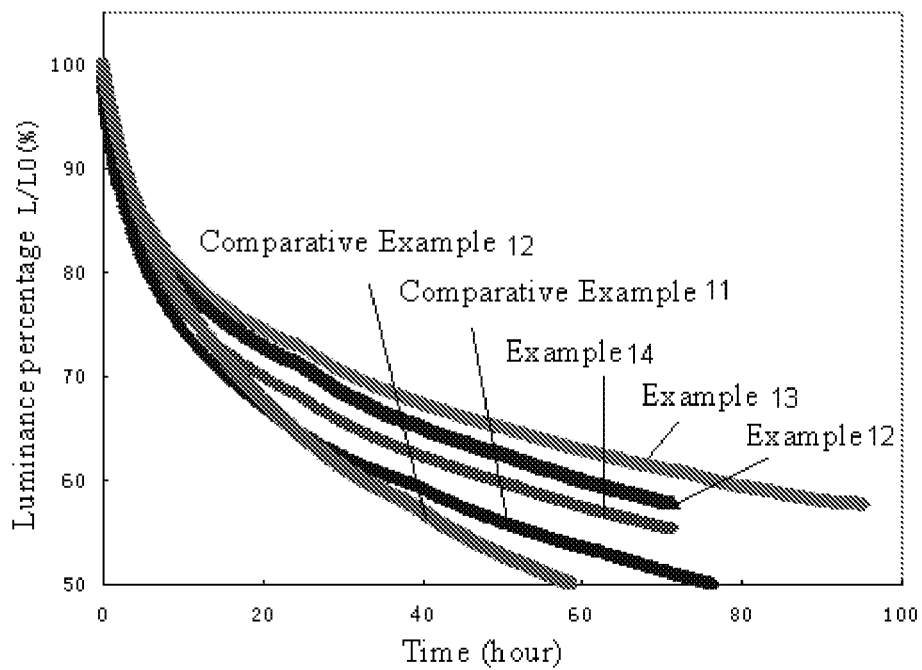
FIG. 4 is a graph illustrating life of light emitting apparatuses of Examples 12 to 14 and Comparative Examples 11 to 12.

The structural general formula of the organic material of the present invention is as follows:

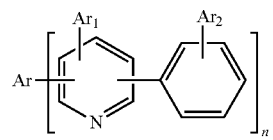

wherein Ar is selected from residues of C6-C30 fused-ring aromatic hydrocarbons, $Ar_1$ and $Ar_e$ are each independently selected from the group consisting of hydrogen, C6-C24 aryl, and C6-C24 heterocyclic aryl, and n is an integer selected from 2 and 3.

In particular, the structural general formulae of the compounds of the present invention are as follows:

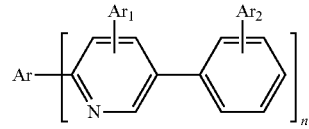
(2)

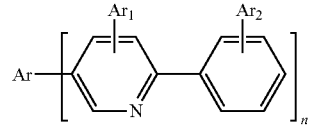
(3)

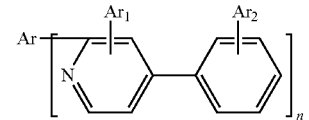
(4)

(5)

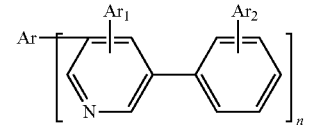
(6)

(7)

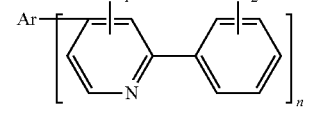

wherein Ar is selected from residues of C6-C30 fused-ring aromatic hydrocarbons, $Ar_1$ and $Ar_2$ are each independently selected from the group consisting of hydrogen, C6-C24 aryl, and C6-C24 heterocyclic aryl, and n is an integer selected from 2 and 3.

In order to illustrate the present invention more clearly, preferable structures of the compounds involved in the present invention are provided as follows.
(1) When n is 2, the structures of some main electron transport materials are as follows.
2-1
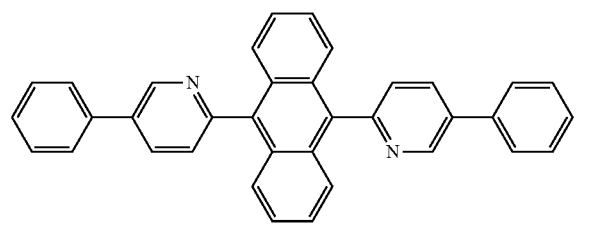
2-2
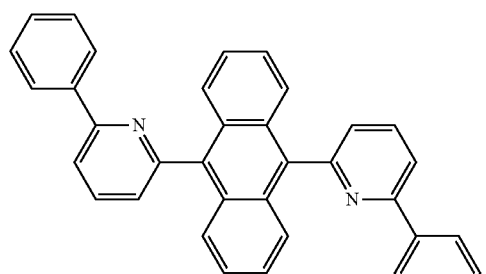
2-3
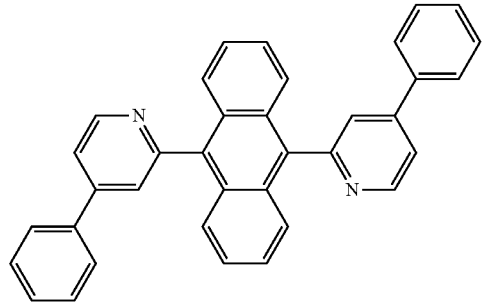
2-4
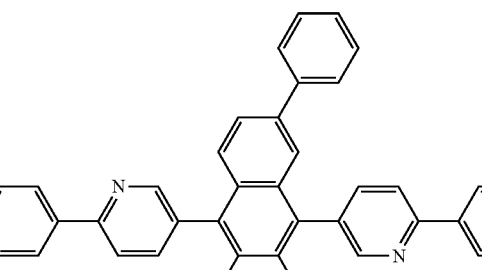
2-5
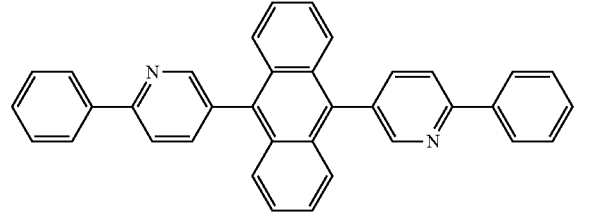
2-6
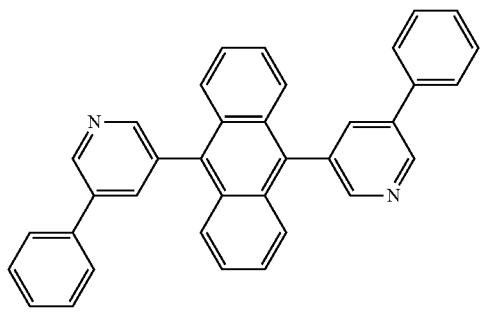
2-7
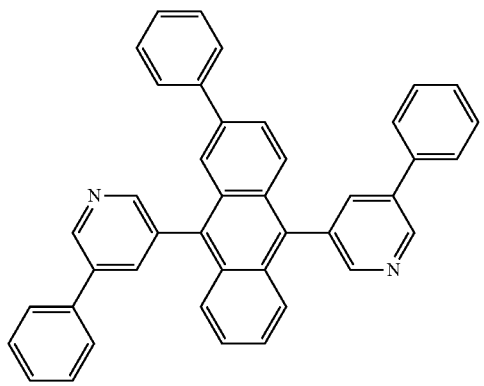
2-8
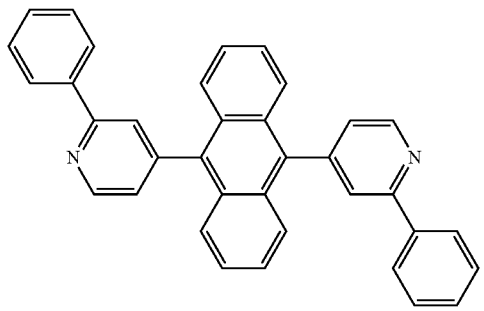
2-9
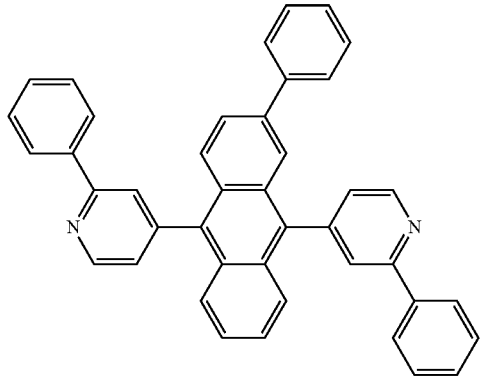

2-10
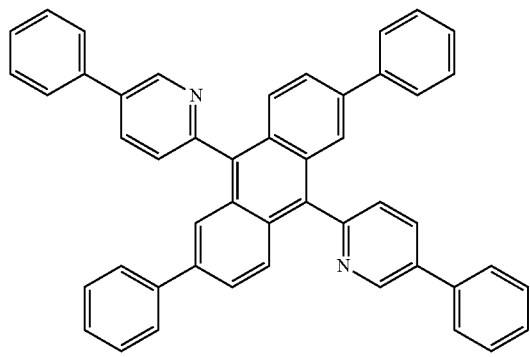
2-11
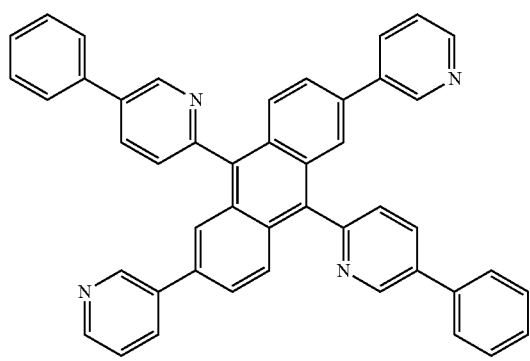
2-12
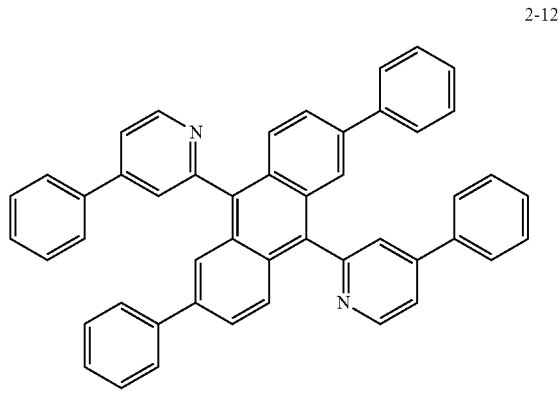
2-13
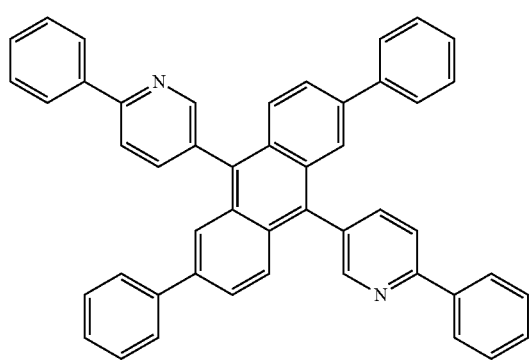
2-14
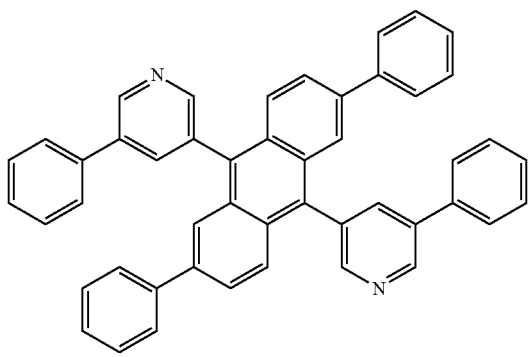
2-15
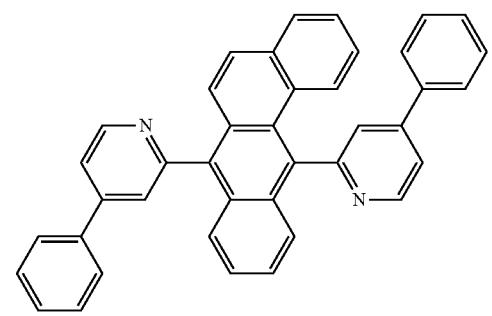
2-16
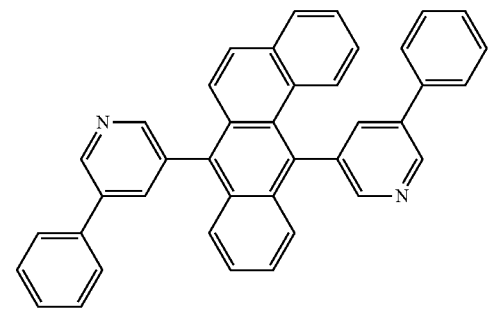
2-17
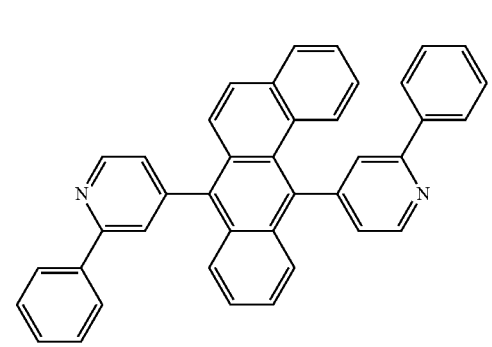

2-18
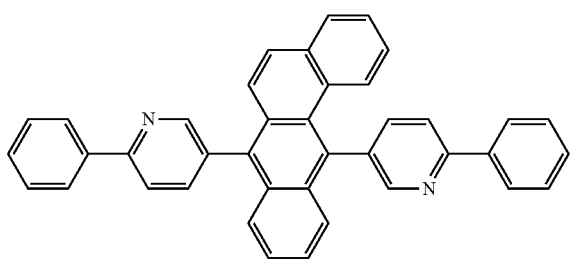
2-23
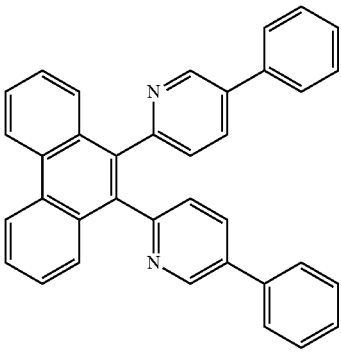
2-19
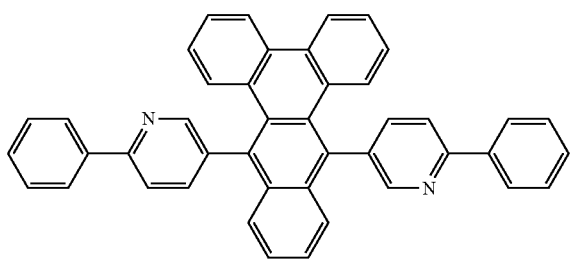
2-24
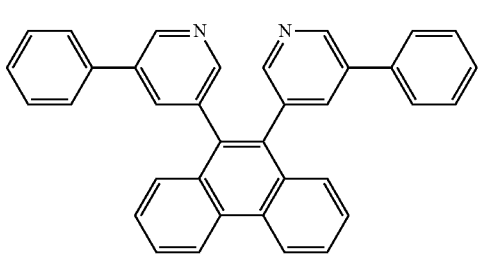
2-20
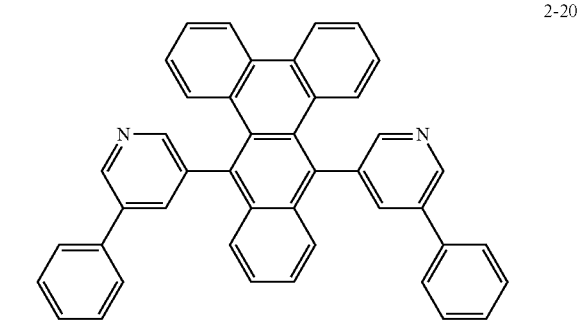
2-25
2-21
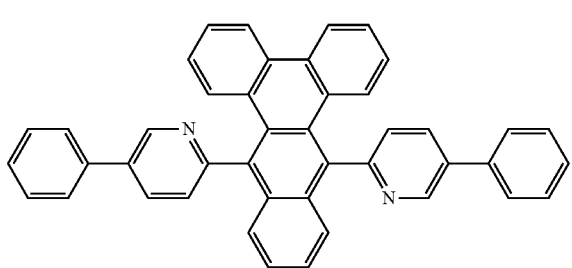
2-26
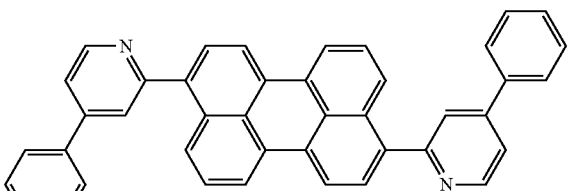
2-27
2-22
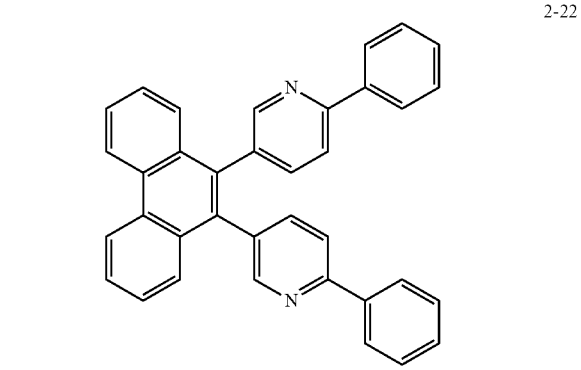
2-28
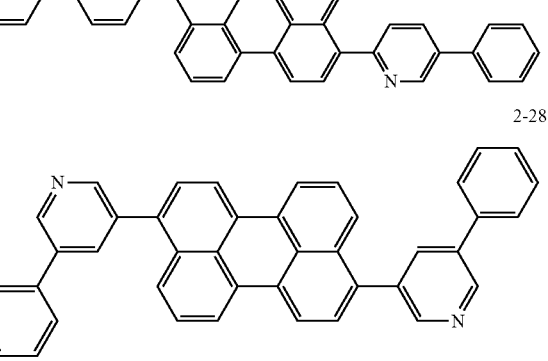

2-29
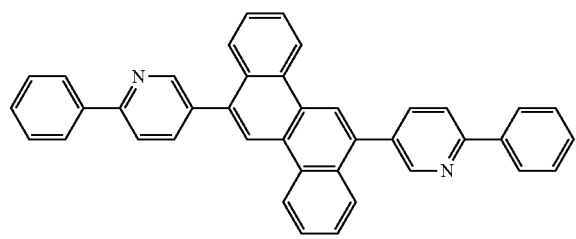
2-30
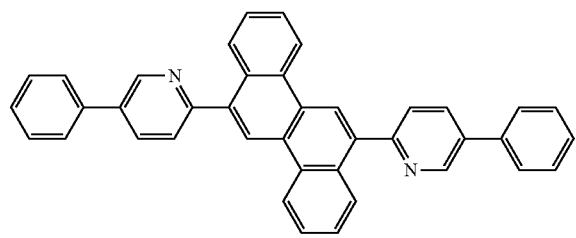
2-31
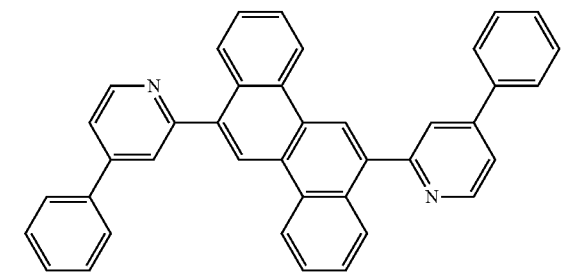
2-32
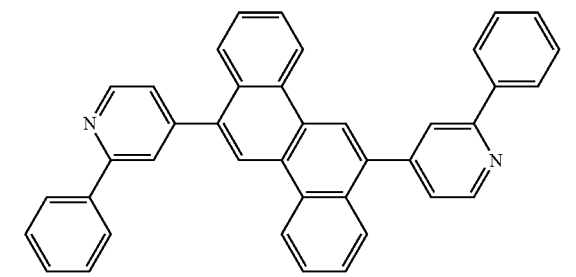
2-33
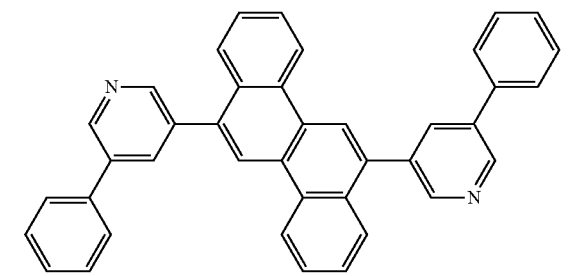
2-34
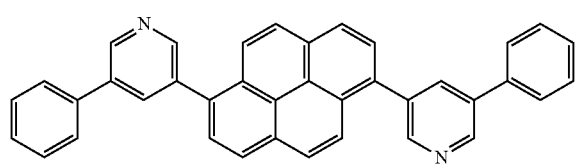
2-35
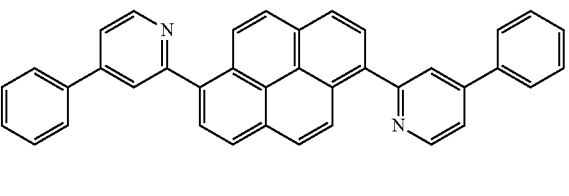
2-36
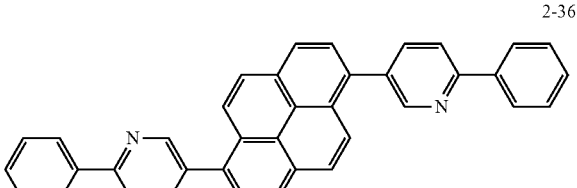
2-37
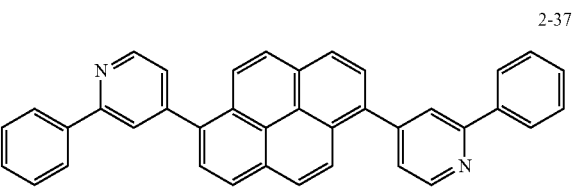
2-38
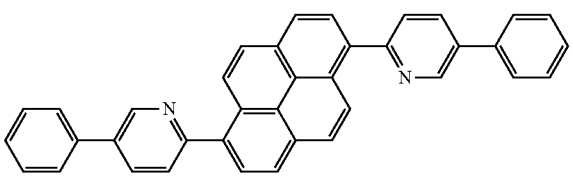
(1) When n is 3, the structures of typical electron transport materials are as follows.
3-1
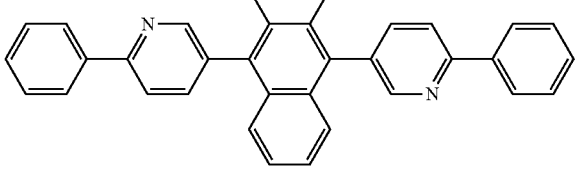

-continued

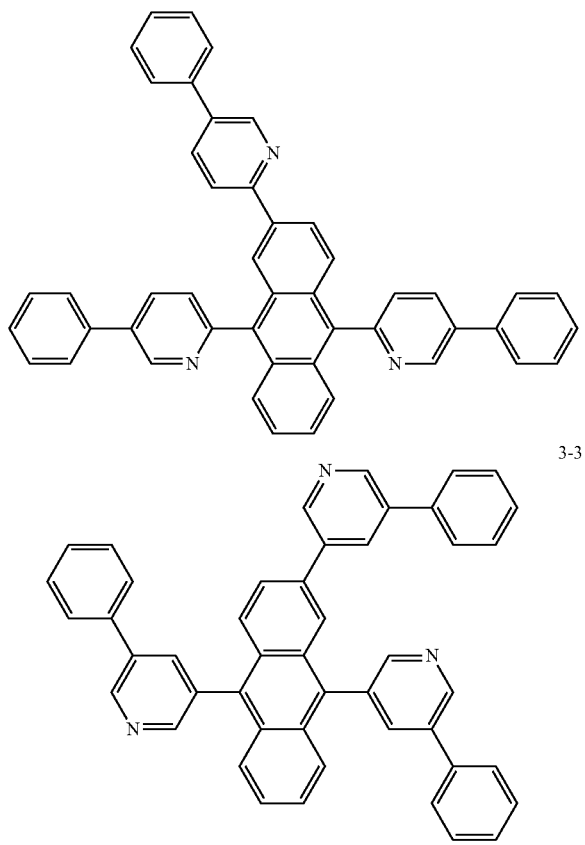

3-2

3-3

The present invention further relates to a novel organic electroluminescent apparatus having better performance.

The organic electroluminescent apparatus of the present invention employs the above novel compound as an electron transport material, has suitable HOMO and LUMO levels, has higher electron injection ability and electron transport ability, enhances ability of supplying electrons to luminescent region, thus significantly reduces driving voltage of the apparatus and improve luminance and luminous efficiency.

The organic electroluminescent apparatus of the present invention employs he above novel compound, and at the same time, can select other suitable material and optimize the structure of the apparatus, to achieve a combination of two functional layers, an electron transport layer and a hole blocking layer, and prevent accelerated deterioration due to holes entering the cathode while ensuring efficient electron transport. Thus, the highly efficient and stable organic electroluminescent apparatus can be obtained.

The organic electroluminescent apparatus of the present invention simultaneously selects a reducing material matchable with the above novel compound as a dopant, which can further reduce barrier of electron injection and enhance efficiently of electron injection. Meanwhile, the dopant is dispersed in the host material of the compound of the present invention, which can weaken interaction among the molecules and perform function of increasing stability of the apparatus and improving life of the apparatus. On the other hand, a buffer layer is disposed between a luminescent layer and an electron inject and transport functional layer, and an organic material having electron transport property can be selected as the material for the buffer layer, which can separate the luminescent layer from the reducing dopant in space, thus preventing the dopant from diffusing into the luminescent region to form luminescent quenching center. Therefore, the buffer layer is beneficial to further enhance stability of the apparatus and prolong life of the apparatus. The material having electron transport property as the first choice for the buffer layer can ensure driving voltage, efficiency and the like of the apparatus to satisfy the requirement for practicability without bringing new burden to the performance of the apparatus.

The organic electroluminescent apparatus of the present invention employs the above new compound doped with an active metal as an N-type layer in connection layers. Preferably, N/P connection layers connect two or more luminescent units as a charge generating layer. Current efficiency of the apparatus in which n luminescent units are stacked is n times than that of the apparatus having a single unit, while its driving voltage is n or less times than that of the apparatus having the single unit. Thus, power efficiency of the apparatus of the present invention is improved to a certain extent.

In addition, the material of the present invention has higher glass transition temperature and higher stability. The material has lower molecular weight and lower thin film deposition temperature, which is beneficial to form a uniform and dense thin film by thermal deposition with a relative simple preparation process.

The present invention also provides an organic electroluminescent apparatus comprising a pair of electrodes and an organic luminescent medium disposed between the pair of electrodes, the organic luminescent medium comprising the novel material the present invention selected from the above general formulae.

The above luminescent medium in the organic apparatus of the present invention comprise a luminescent layer and an electron transport functional layer, wherein the above novel material of the present invention is used in said electron transport functional layer.

The above electron transport functional layer further contain another electron transport material which is selected from the group consisting of oxazole compounds, metal chelates, triazole compounds, imidazole compounds, phenanthroline compounds or anthracene compounds.

The above oxazole compounds, metal chelates, triazole compounds, imidazole compounds, phenanthroline compounds or anthracene compounds includes: 2-(4-tertbutylphenyl)-5-(4-biphenyl)-1,3,4-oxadiazole, tris(8-hydroxyquinolato)aluminum, 3-(4-biphenyl)-4-phenyl-5-(4-butylphenyl)-1,2,4-triazole, 4,7-diphenyl-1,10-phenanthroline, 2,9-dimethyl-4,7-diphenyl-1,10-phenanthroline, and 2-phenyl-9,10-dinaphthylanthracene.

The above electron transport layer comprising two electron transport materials is further doped with alkaline metals, alkaline metal oxides, alkaline metal halides, alkaline metal nitrides, alkaline metal salts.

The above dopant is selected from the group consisting of lithium, cesium, lithium nitride, lithium fluoride, lithium cobaltate, lithium oxide, 8-hydroxyquinolato lithium, cesium carbonate, potassium borohydride, lithium borohydride, sodium fluoride, sodium chloride, cesium fluoride, cesium chloride, and rubidium oxide.

The doping concentration of the above dopant in the electron transport functional layer is in the range of 1% to 49%, based on the weight of the host material.

The above luminescent medium in the organic apparatus of the present invention comprise a luminescent layer and an electron inject and transport functional layer, wherein said electron inject and transport functional layer contains the above novel compound of the present invention, and at the same time, further contains a dopant, the dopant is selected from the group consisting of alkaline metals, alkaline metal oxides, alkaline metal halides, alkaline metal nitrides, and alkaline metal salts.

The above dopant is selected from the group consisting of lithium, cesium, lithium nitride, lithium fluoride, lithium cobaltate, lithium oxide, 8-hydroxyquinolato lithium, cesium carbonate, potassium borohydride, lithium borohydride, sodium fluoride, sodium chloride, cesium fluoride, cesium chloride, and rubidium oxide.

The above electron injection and transport functional layer has a thickness in the range of 2 nm to 5 nm, preferable in the range of 5 nm to 25 nm. The doping ratio of the dopant in the electron injection and transport layer is in the range of 0.1% to 49% by weight, preferably in the range of 0.5% to 30% by weight.

In the above organic electroluminescent apparatus of the present invention, a buffer layer is disposed between the electron inject and transport layer and the luminescent layer. The material for the buffer layer is selected from the above novel compounds of the present invention, or selected from the group consisting of oxazole compounds, metal complexes, triazole compounds, imidazole compounds, quinoline compounds, oxaline (quinoxaline) compounds, phenazine compounds, and phenanthroline compounds.

The material for the buffer layer is preferably selected from the group consisting of the above compounds 2-1 to 2-38 and 3-1 to 3-3 of the present invention, or selected from the group consisting of 2-(4-tertbutylphenyl)-5-(4-biphenyl)-1,3,4-oxadiazole, tris(8-hydroxyquinolato)aluminum, 3-(4-biphenyl)-4-phenyl-5-(4-butylphenyl)-1,2,4-triazole, 4,7-diphenyl-1,10-phenanthroline, 2,9-dimethyl-4,7-diphenyl-1,10-phenanthroline, and 2-phenyl-9,10-dinaphthylanthracene.

The above buffer layer has a thickness in the range of 2 nm to 20 nm.

In the above organic electroluminescent apparatus of the present invention, the organic luminescent medium comprises at least two luminescent units with a connection layer disposed between the luminescent units, wherein the connection layer contains the above novel compound of the present invention.

A dopant selected from the group consisting of alkaline metals, alkaline metal oxides, alkaline metal halides, alkaline metal nitrides, and alkaline metal salts is doped in the above connection layer. The dopant is preferably selected from the group consisting of lithium, cesium, lithium nitride, lithium fluoride, lithium cobaltate, lithium oxide, 8-hydroxyquinolato lithium, cesium carbonate, potassium borohydride, lithium borohydride, sodium fluoride, sodium chloride, cesium fluoride, cesium chloride, and rubidium oxide.

Examples of Methods for Synthesizing Materials

All the basic chemical raw materials such as various pyridyl boric acids, phenyl pyridyl boric acids, pyridyl phenyl boric acid, bromoanthracenes, bromoperylenes, bromonaphthalenes, anthraquinones, benzoanthraquinones, dibenzoanthracene and the like used in the present invention are easily available in the chemical product market. Each of phenyl pyridyl boric acids can be synthesized by using common organic methods.

All the basic chemical raw materials such as various bromoiodopyridine, anthraquinones, benzoanthraquinones, dibenzoanthracene and the like used in the present invention are easily available in the domestic chemical product market. Each of bromoanthracenes, bromoperylenes, and phenyl pyridyl boric acids can be synthesized by using common organic methods.

EXAMPLES

The methods for synthesizing a part of the main compounds in the present invention are illustrated as follows.

Synthesis Example 1

Synthesis of Compound 2-1

(1) Reaction of the First Step

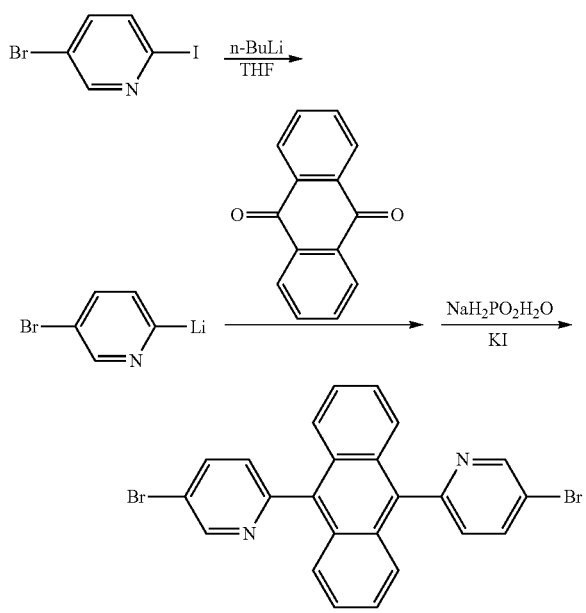

After argon replacement in a three-neck bottle of 500 ml equipped with magnetic stirrer, 13.4 g of 2-iodo-5-bromopyridine (purity of 99%, 0.0473 mol) and 200 ml of THF are sequentially added thereto. 19 ml of n-butyl lithium (concentration of 2.5 M, 0.0475 mol) is dropwise added at −83° C., and then 4.8 g of anthraquinone (purity of 99%, 0.023 mol) is immediately added. After addition, the temperature is naturally raised to room temperature, and the solution exhibits bright yellow color. 200 ml of water is added for hydrolysis, the resultant is extracted with ethyl acetate, and the solvent is evaporated. After adding 300 ml of acetic acid, 18 g of KI and 18 g of sodium hypophosphite, the resultant is refluxed and allowed to react for 1 hour. Then, the temperature is reduced, acetic acid is evaporated, and the resultant is washed with water. Thus, 5.05 g of yellow compound is obtained with purity of 87.42% and yield of 39.19%.

(2) Reaction of the Second Step

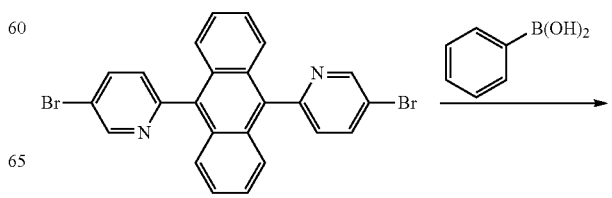

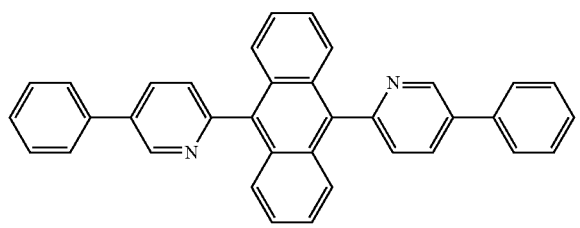

Under protection of N$_2$ gas, 6.0 g of 9,10-di(5-bromopyrid-2-yl)anthracene (molecular weight of 490, purity of 87.42%, 0.0106 mol), 3.73 g of phenyl boric acid (purity of 98%, 0.03 mol), 0.21 g of palladium chloride (purity of AR, 0.00124 mol), 0.63 g of triphenylphosphine (purity of AR, 0.0024 mol), 5.3 g of potassium carbonate (purity of AR, 0.0486 mol), 86 ml of toluene, 60 ml of ethanol, and 72 ml of water are added into a three-neck bottle of 500 ml. The above materials are heated to reflux, and phenyl boric acid is supplemented twice (1 g once). The reaction is stopped after 4 hours. The resultant is cooled and filtered. The filter cake is boiled in toluene with heating and filtered. Then, the catalyst is removed, and toluene is evaporated. The solid obtained is boiled in water/THF with a ratio of 1/10, cooled and filtered, which are repeated twice. Thus, 4.1 g of grey compound 2-1 is obtained with purity of 99.14% and yield of 77.97%.

Mass Spectrum (MS) of the product (m/e): 484; Elemental analysis (C$_{36}$H$_{24}$N$_2$): Theoretical, C: 89.23%, H: 4.99%, N: 5.78%; Measured, C: 89.10%, H: 5.08%, N: 5.82%.

Synthesis Example 2

Synthesis of Compound 2-3

The pale yellow compound 2-3 is obtained by using anthraquinone, 2-iodo-4-bromopyridine and phenyl boric acid via the same two-step reaction as in the Example 1.

Mass Spectrum (MS) of the product (m/e): 484; Elemental analysis (C$_{36}$H$_{24}$N$_2$): Theoretical, C: 89.23%, H: 4.99%, N: 5.78%; Measured, C: 89.21%, H: 5.05%, N: 5.74%.

Synthesis Example 3

Synthesis of Compound 2-5

(1) Reaction of the First Step

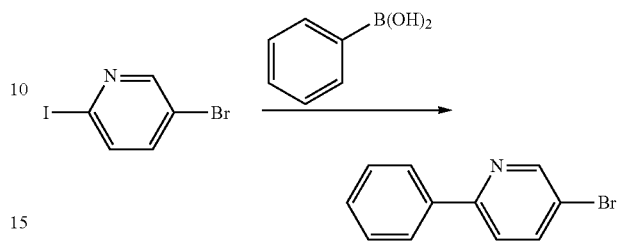

After argon replacement in a three-neck bottle of 500 ml equipped with magnetic stirrer, 8.26 g of 2-iodo-5-bromopyridine (purity of 99%, 0.0288 mol), 3.58 g of phenyl boric acid (purity of 98%, 0.0292 mol), 1.79 g of Pd(PPh$_3$)$_4$ (AR, 0.00155 mol), 175 ml of aqueous solution of sodium carbonate (concentration of 2M), 175 ml of benzene, and 175 ml of ethanol are sequentially added thereto, refluxed, and allowed to react for 2 hours. The temperature is reduced, and the organic layer is separated and evaporated. The resultant is subjected to column separation with ethyl acetate/petroleum ether in a ratio of 1/20. Thus, 6.75 g of product is obtained with purity of 95.45% and yield of 94.43%.

(2) Reaction of the Second Step

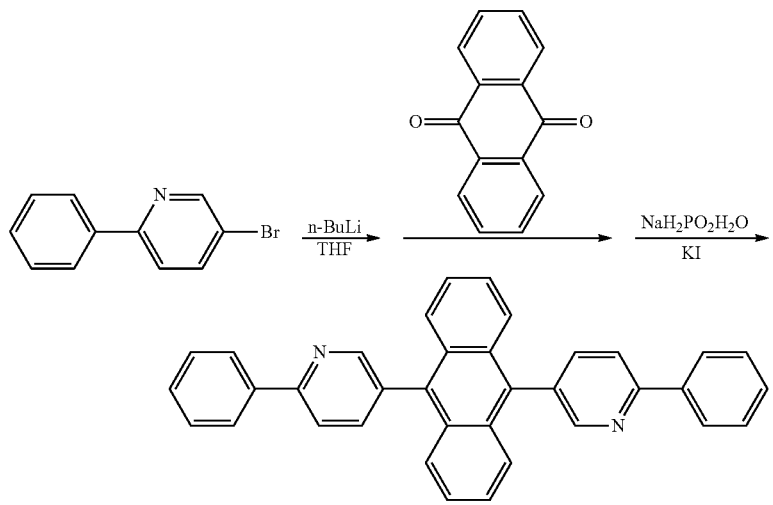

After nitrogen replacement in a three-neck bottle of 500 ml equipped with magnetic stirrer, 6.75 g of 2-phenyl-5-bromopyridine (purity of 95.45%, 0.0274 mol) and 110 ml of THF are sequentially added thereto. 13 ml of n-butyl lithium (concentration of 2.5 M, 0.0325 mol) is dropwise added at −70° C. After agitation for 10 minutes, 2.6 g of anthraquinone (purity of 99%, 0.0124 mol) is added. After addition, the temperature is naturally raised to room temperature, and the solution exhibits bright yellow color. 200 ml of water is added for hydrolysis, the resultant is extracted with ethyl acetate, and the solvent is evaporated. After adding 220 ml of acetic acid, 22 g of KI and 22 g of sodium hypophosphite, the resultant is refluxed and allowed to react for 1 hour. Then, the temperature is reduced, and the resultant is filtered to obtain 2.8 g of pale yellow product. The pale yellow product is boiled in water/THF with a ratio of 15/100, cooled and filtered, which are repeated for several times. Thus, 2.1 g of pale white compound 2-5 is obtained with purity of 99.0% and yield of 20.48%.

Mass Spectrum of the product (MS) (m/e): 484; Elemental analysis ($C_{36}H_{24}N_2$): Theoretical, C: 89.23%, H: 4.99%, N: 5.78%; Measured, C: 89.30%, H: 5.01%, N: 5.69%.

Synthesis Example 4

Synthesis of Compound 2-7

The pale yellow compound 2-7 is obtained by using 2-phenylanthraquinone and 3,5-bromopyridine via the same two-step reaction as in the Example 3. Mass Spectrum (MS) of the product (m/e): 560; Elemental analysis ($C_{42}H_{28}N_2$): Theoretical, C: 89.97%, H: 5.03%, N: 5.00%; Measured, C: 89.91%, H: 5.06%, N: 5.03%.

Synthesis Example 5

Synthesis of Compound 2-9

The pale yellow compound 2-9 is obtained by using anthraquinone and 2-phenyl-4-bromopyridine via the same reaction as in the Example 3. Mass Spectrum (MS) of the product (m/e): 560; Elemental analysis ($C_{42}H_{28}N_2$): Theoretical, C: 89.97%, H: 5.03%, N: 5.00%; Measured, C: 89.98%, H: 5.05%, N: 4.97%.

Synthesis Example 6

Synthesis of Compound 2-11

The yellow compound 2-11 is obtained by using 2,6-di(3-pyridyl)anthraquinone and 2-iodo-5-bromopyridine via the same reaction as in the Example 1. Mass Spectrum (MS) of the product (m/e): 638; Elemental analysis ($C_{46}H_{30}N_4$): Theoretical, C: 86.49%, H: 4.73%, N: 8.77%; Measured, C: 86.40%, H: 4.79%, N: 8.81%.

Synthesis Example 7

Synthesis of Compound 2-13

The pale yellow compound 2-13 is obtained by using 2,6-diphenylanthraquinone and 2-iodo-5-bromopyridine via the same reaction as in the Example 3. Mass Spectrum (MS) of the product (m/e): 636; Elemental analysis ($C_{48}H_{32}N_4$): Theoretical, C: 90.53%, H: 5.07%, N: 4.40%; Measured, C: 90.50%, H: 5.12%, N: 4.38%.

Synthesis Example 8

Synthesis of Compound 2-15

The yellow compound 2-15 is obtained by using benzoanthraquinone and 4-phenyl-2-bromopyridine via the same second step reaction as in the Example 3. Mass Spectrum (MS) of the product (m/e): 534; Elemental analysis ($C_{40}H_{26}N_2$): Theoretical, C: 89.86%, H: 4.90%, N: 5.24%; Measured, C: 89.80%, H: 4.91%, N: 5.29%.

Synthesis Example 9

Synthesis of Compound 2-18

The yellow compound 2-18 is obtained by using benzoanthraquinone and 2-iodo-5-bromopyridine via the same reaction as in the Example 3. Mass Spectrum (MS) of the product (m/e): 534; Elemental analysis ($C_{40}H_{26}N_2$): Theoretical, C: 89.86%, H: 4.90%, N: 5.24%; Measured, C: 89.85%, H: 4.82%, N: 5.33%.

Synthesis Example 10

Synthesis of Compound 2-19

The yellow compound 2-19 is obtained by using dibenzoanthraquinone and 2-iodo-5-bromopyridine via the same reaction as in the Example 3. Mass Spectrum (MS) of the product (m/e): 584; Elemental analysis ($C_{44}H_{28}N_2$): Theoretical, C: 90.38%, H: 4.83%, N: 4.79%; Measured, C: 90.34%, H: 4.90%, N: 4.76%.

Synthesis Example 11

Synthesis of Compound 2-21

The yellow compound 2-21 is obtained by using dibenzoanthraquinone and 2-iodo-5-bromopyridine via the same reaction as in the Example 1. Mass Spectrum (MS) of the product (m/e): 584; Elemental analysis ($C_{44}H_{28}N_2$): Theoretical, C: 90.38%, H: 4.83%, N: 4.79%; Measured, C: 90.46%, H: 4.70%, N: 4.84%.

Synthesis Example 12

Synthesis of Compound 2-23

The yellow compound 2-23 is obtained by using phenanthraquinone and 2-iodo-5-bromopyridine via the same reaction as in the Example 1. Mass Spectrum (MS) of the product (m/e): 484; Elemental analysis ($C_{36}H_{24}N_2$): Theoretical, C: 89.23%, H: 4.99%, N: 5.78%; Measured, C: 89.40%, H: 4.85%, N: 5.75%.

Synthesis Example 13

Synthesis of Compound 2-25

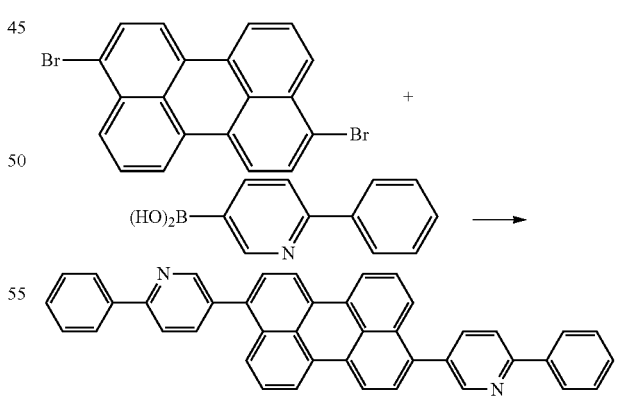

Under protection of $N_2$ gas, 4.32 g of 3,9-dibromoperylene (purity of 95%, 0.01 mol), 5.1 g of 6-phenylpyridyl-3-boric acid (purity of 98%, 0.025 mol), 0.21 g of palladium chloride (purity of AR, 0.0012 mol), 0.63 g of triphenylphosphine (purity of AR, 0.0024 mol), 5.3 g of potassium carbonate (purity of AR, 0.0486 mol), 86 ml of toluene, 60 ml of ethanol, and 72 ml of water are added into a three-neck bottle of 500 ml. The above materials are heated to reflux. The reaction is stopped after 4 hours. The resultant is cooled and filtered. The filter cake is boiled in toluene with heating and filtered. Then, the catalyst is removed, and toluene is evaporated. The solid obtained is boiled in water/THF with a ratio of 1/10, cooled and filtered, which are repeated twice. Thus, 4.2 g of offwhite product is obtained with purity of 99.10% and yield of 75.26%.

Mass Spectrum (MS) of the product (m/e): 558; Elemental analysis ($C_{42}H_{26}N_2$): Theoretical, C: 90.29%, H: 4.69%, N: 5.01%; Measured, C: 90.11%, H: 4.88%, N: 5.01%.

Synthesis Example 14

Synthesis of Compound 2-28

The yellow compound 2-28 is obtained by using 3,9-dibromoperylene and 5-phenylpyridyl-3-boric acid via the same reaction as in the Example 13. Mass Spectrum (MS) of the product (m/e): 558; Elemental analysis ($C_{42}H_{26}N_2$): Theoretical, C: 90.29%, H: 4.69%, N: 5.01%; Measured, C: 90.11%, H: 4.88%, N: 5.01%.

Synthesis Example 15

Synthesis of Compound 2-31

The yellow compound 2-31 is obtained by using 6,12-dibromochrysene and 6-phenylpyridyl-3-boric acid via the same reaction as in the Example 13. Mass Spectrum (MS) of the product (m/e): 534; Elemental analysis ($C_{40}H_{26}N_2$): Theoretical, C: 89.96%, H: 4.90%, N: 5.24%; Measured, C: 90.01%, H: 4.86%, N: 5.13%.

Synthesis Example 16

Synthesis of Compound 2-33

The yellow compound 2-33 is obtained by using 6,12-dibromochrysene and 5-phenylpyridyl-3-boric acid via the same reaction as in the Example 13. Mass Spectrum (MS) of the product (m/e): 534; Elemental analysis ($C_{40}H_{26}N_2$): Theoretical, C: 89.96%, H: 4.90%, N: 5.24%; Measured, C: 89.80%, H: 4.93%, N: 5.27%.

Synthesis Example 17

Synthesis of Compound 2-35

The yellow compound 2-35 is obtained by using 1,6-dibromopyrene and 4-phenylpyridyl-2-boric acid via the same reaction as in the Example 13. Mass Spectrum (MS) of the product (m/e): 508; Elemental analysis ($C_{38}H_{24}N_2$): Theoretical, C: 89.74%, H: 4.76%, N: 5.51%; Measured, C: 89.81%, H: 4.70%, N: 5.49%.

Synthesis Example 18

Synthesis of Compound 2-37

The yellow compound 2-37 is obtained by using 1,6-dibromopyrene and 2-phenylpyridyl-4-boric acid via the same reaction as in the Example 13. Mass Spectrum (MS) of the product (m/e): 508; Elemental analysis ($C_{38}H_{24}N_2$): Theoretical, C: 89.74%, H: 4.76%, N: 5.51%; Measured, C: 89.70%, H: 4.81%, N: 5.49%.

Synthesis Example 19

Synthesis of Compound 3-1

The pale yellow compound 3-1 is obtained by using 2,9,10-tribromoanthracene and 2-phenylpyridyl-4-boric acid via the same reaction as in the Example 13. Mass Spectrum (MS) of the product (m/e): 637; Elemental analysis ($C_{47}H_{31}N_3$): Theoretical, C: 88.51%, H: 4.90%, N: 6.59%; Measured, C: 88.49%, H: 4.95%, N: 6.56%.

Synthesis Example 20

Synthesis of Compound 3-3

The pale yellow compound 3-3 is obtained by using 2,9,10-tribromoanthracene and 6-phenylpyridyl-3-boric acid via the same reaction as in the Example 13. Mass Spectrum (MS) of the product (m/e): 637; Elemental analysis ($C_{47}H_{31}N_3$): Theoretical, C: 88.51%, H: 4.90%, N: 6.59%; Measured, C: 88.55%, H: 4.93%, N: 6.52%.

Examples of Organic Electroluminescent Apparatuses

The basic structure of the organic electroluminescent apparatus proposed in the present invention includes: a substrate, a pair of electrodes, and an organic medium disposed between the electrodes, the organic medium including a hole inject layer, a hole transport layer, a luminescent layer, an electron transport layer, an electron inject layer, a blocking layer and the like.

The substrate is a transparent substrate which can be glass or flexible substrate, wherein the flexible substrate can employ a material of polyester compounds and polyimide compounds. The first electrode layer (anode layer) can employ an inorganic material or an organic conductive polymer, wherein the inorganic material is generally metal oxide such as ITO, zinc oxide, tin zinc oxide and the like or metal having a higher work function such as gold, copper, silver and the like, and most preferably ITO, and the organic conductive polymer is preferably a material of polythiophene/sodium polystyrene sulfonate (below abbreviated as PEDOT:PSS) and polyaniline (below abbreviated as PANI). The second electrode layer (cathode layer, metal layer) generally either employs metal having a lower work function such as lithium, magnesium, calcium, strontium, aluminum, indium and the like, or alloy of the metal having a lower work function with copper, gold, or silver, or employs electrode layers alternately formed of metal and metal fluoride. Preferably, the second electrode layer in the present invention is successive Mg:Ag alloy layer and Ag layer, and successive LiF layer and Al layer.

The organic luminescent medium mainly includes an organic electroluminescent layer (EML). EML generally employs a small molecule material which can be a fluorescent material such as compounds of organic metal complex type (e.g., $Alq_3$, $Gaq_3$, Al(Saph-q) or Ga(Saqh-q)). The small molecule material can be doped with dye in a doping concentration of 0.01 wt % to 20 wt % of the small molecule material. The dye generally is a material of aromatic fused-ring series (e.g., rubrene), coumarin series (e.g., DMQA, C545T), or dipyran series (e.g., DCJTB, DCM). The material for EML also can employ carbazole compounds such as 4,4'-N,N'-dicarbazolyl-bipheyl (CBP), polyvinyl carbazole (PVK). The material can be doped with a phosphorescent dye such as tris(-phenylpyridine) iridium (Ir(ppy)₃), di(2-phenylpyridine)(acetylacetonate) iridium (Ir(ppy)₂(acac)), octaethylporphyrin platinum (PtOEP) and the like.

The hole injection layer and the hole transport layer can also be included in the structure of the above apparatus. The host material for the hole inject layer (HIL) can employ copper phthalocyanine (CuPc), 4,4',4"-tris(N-3-methylphenyl-N-phenyl-amino)-triphenylamine (m-MTDATA), 4,4',4"-tris(N-2-naphthyl-N-phenyl-amino)-triphenylamine (2-TNATA).

The material for the hole transport layer can employ N,N'-bis-(1-naphthyl)-N,N'-diphenyl-1,1'-biphenyl-4,4'-diamine (NPB), TPD and the like.

The material for the electron inject and transport layer in the apparatus employs the material of the present invention.

Several materials used in the present invention are as follows.

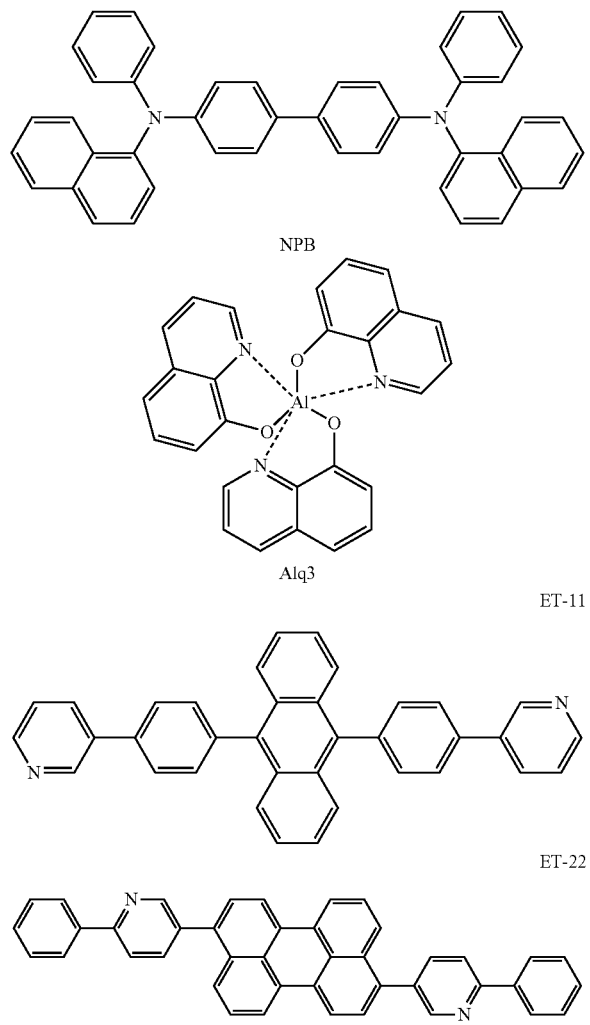

Several Examples will be provided below to explain the embodiments of the present invention in detail in combination with the figures. It should be noted that the Examples below is only intended to help understanding the present invention and is not limiting of the present invention.

Design of Apparatus: in order to easily compare transport properties of these electron transport materials, the present invention designs a simple organic electroluminescent apparatus (substrate/anode/hole transport layer (HTL)/organic luminescent layer (EML)/electron transport layer (ETL)/cathode), wherein the luminescent layer employs 9,10-di(2-naphthyl)anthracene (ADN) as an example of luminescent material (ADN is a host material instead of a luminescent material, and its object is not to seek high efficiency, but to verify possibility of practice of these materials).

Example 1

Structure of apparatus: ITO/NPB (40 nm)/ADN (30 nm)/Compound 2-1 (20 nm)/LiF (0.5 nm)/Al (150 nm)

A glass substrate coated with ITO transparent conductive layer is subjected to ultrasonic treatment in a commercial cleaning agent, rinsed in deionized water, ultrasonically deoiled in a mixed solvent of acetone and ethanol, baked in a clean environment until complete removal of moisture, and purged with ultraviolet light and ozone, and then its surface is bombarded by low energy cation beam.

The above glass substrate with the anode is placed in a vacuum chamber and evacuated to $1\times10^{-5}\sim9\times10^{-3}$ Pa. NPB is vacuum deposited on the above anode layer as a hole transport layer with a deposition rate of 0.1 nm/s and a deposition film thickness of 50 nm.

ADN is vacuum deposited on the hole transport layer as a luminescent layer in the apparatus with a deposition rate of 0.1 nm/s and an overall thickness of deposition film of 30 nm.

The Compound 2-1 of the present invention is vacuum deposited on the luminescent layer as an electron transport layer in the apparatus with a deposition rate of 0.1 nm/s and an overall thickness of deposition film of 20 nm.

LiF is vacuum deposited on the electron transport layer to a thickness of 0.5 nm as an electron inject layer, and finally Al metal is coated by thermal deposition as a cathode with a thickness of 150 nm.

Example 2

Structure of apparatus: ITO/NPB (40 nm)/ADN (30 nm)/Compound 2-3 (30 nm)/LiF (0.5 nm)/Al (150 nm)

The apparatus is prepared according to the manner in the Example 1, except that the electron transport layer employs the Compound 2-3 of the present invention and has a thickness of 30 nm. LiF with a thickness of 0.5 nm is deposited thereon as an electron inject layer, and finally Al metal is coated by thermal deposition as a cathode with a thickness of 150 nm.

Comparative Example 1

Structure of apparatus: ITO/NPB (40 nm)/ADN (30 nm)/Alq₃ (20 nm)/LiF (0.5 nm)/Al (150 nm)

The apparatus is prepared according to the manner in the Example 1, except that the electron transport layer employs Alq₃ and has a thickness of 20 nm.

Comparative Example 2

Structure of apparatus: ITO/NPB (40 nm)/ADN (30 nm)/Alq₃ (30 nm)/LiF (0.5 nm)/Al (150 nm)

The apparatus is prepared according to the manner in the Example 1, except that the electron transport layer employs Alq₃ and has a thickness of 30 nm.

Comparative Example 3

Structure of apparatus: ITO/NPB (40 nm)/ADN (30 nm)/ET-11 (20 nm)/LiF (0.5 nm)/Al (150 nm)

The apparatus is prepared according to the manner in the Example 1, except that the electron transport layer employs ET-11 and has a thickness of 20 nm.

TABLE 1

|  | Material used | Voltage at 1000 cd/m² V | Current efficiency at 1000 cd/m² cd/A | x | y |
|---|---|---|---|---|---|
| Example 1 | Compound 2-1 (20 nm) | 8.14 | 0.97 | 0.1997 | 0.2525 |
| Example 2 | Compound 2-3 (30 nm) | 9.95 | 1.02 | 0.1858 | 0.2620 |
| Comparative Example 1 | Alq₃ (20 nm) | 10.76 | 0.82 | 0.1927 | 0.2623 |
| Comparative Example 2 | Alq₃ (30 nm) | 11.58 | 0.78 | 0.1951 | 0.2611 |
| Comparative Example 3 | ET-11 (20 nm) | 8.16 | 0.90 | 0.1920 | 0.2565 |

It can be seen from Table 1 that as compared with $Alq_3$, when the electron transport layer employs the Compound 2-1 or 2-3, voltage is lower and current efficiency, lumen efficiency and external quantum efficiency are higher at luminance of 1000 cd/m², and no red shift occurs in chromaticity coordinate. Although the thickness of the electron transport layer in the Example 2 increases by 10 nm, the influence on the performance of the apparatus is less. However, when the thickness of the electron transport layer in the Comparative Example 2 also increases by 10 nm, the driving voltage of the apparatus increases significantly and the efficiency decreases. As compared with the Example 1, the Comparative Example 3 employing ET-11 as the electron transport layer has a high driving voltage and a low efficiency. The above results demonstrate that the novel organic material of the present invention can be preferably used as the electron transport layer in the organic electroluminescent apparatus.

Example 3

Structure of apparatus: ITO/NPB (40 nm)/ADN (30 nm): 7% of TBPe/Compound 2-9 (30 nm)/LiF/Al An ITO substrate is treated according to the manner in the Example 1 and placed in a deposition chamber in which a hole inject layer, a hole transport layer, a luminescent layer, an electron transport layer, an electron inject layer and a cathode are successively deposited under a chamber pressure of less than $5.0 \times 10^{-3}$ Pa during deposition. In the present Example, NPB with a thickness of 40 nm is firstly deposited as the hole transport layer, ADN and 2,5,8,11-tetratertbutylperylene (TBPe) with a thickness of 30 nm are deposited as the luminescent layer by a method of double source codeposition wherein a ratio of TBPe in ADN is controlled at 7% by rate, the Compound 2-9 with a thickness of 20 nm is deposited as the electron transport layer, and LiF with a thickness of 0.5 nm and Al with a thickness of 150 nm are deposited respectively as the electron inject layer and the cathode.

Example 4

Structure of apparatus: ITO/NPB (40 nm)/ADN (30 nm): 7% of TBPe/Compound 2-9 (20 nm)/Alq₃ (10 nm)/LiF/Al The apparatus is prepared according to the manner in the Example 3, except that the Compound 2-9 with a thickness of 20 nm and Alq₃ with a thickness of 10 nm are successively deposited on the luminescent layer as the electron transport layer, and finally LiF with a thickness of 0.5 nm and Al with a thickness of 150 nm are deposited respectively as the electron inject layer and the cathode.

Example 5

Structure of apparatus: ITO/NPB (40 nm)/ADN (30 nm): 7% of TBPe/Compound 2-9 (20 nm)/Compound 3-1 (10 nm)/LiF/Al The apparatus is prepared according to the manner in the Example 3, except that the Compound 2-9 with a thickness of 20 nm and the Compound 3-1 with a thickness of 10 nm are successively deposited on the luminescent layer as the electron transport layer, and finally LiF with a thickness of 0.5 nm and Al with a thickness of 150 nm are deposited respectively as the electron inject layer and the cathode.

Comparative Example 4

Structure of apparatus: ITO/NPB (40 nm)/ADN (30 nm): 7% of TBPe/Alq₃ (30 nm)/LiF/Al The apparatus is prepared according to the manner in the Example 3, except that Alq₃ with a thickness of 30 nm are successively deposited on the luminescent layer as the electron transport layer, and finally LiF with a thickness of 0.5 nm and Al with a thickness of 150 nm are deposited respectively as the electron inject layer and the cathode.

Comparative Example 5

Structure of apparatus: ITO/NPB (40 nm)/ADN (30 nm): 7% of TBPe/ET-12 (30 nm)/LiF/Al The apparatus is prepared according to the manner in the Example 3, except that ET-12 with a thickness of 30 nm are successively deposited on the luminescent layer as the electron transport layer, and finally LiF with a thickness of 0.5 nm and Al with a thickness of 150 nm are deposited respectively as the electron inject layer and the cathode.

TABLE 2

|  | Condition | Luminance at 8 V (cd/m²) | Efficiency at 8 V (cd/A) | Current density at 8 V (A/m²) |
|---|---|---|---|---|
| Example 3 | Compound 2-9 (30 nm) | 15,320 | 7.3 | 2,099 |
| Example 4 | Compound 2-9 (20 nm)/Alq₃ (10 nm) | 11,350 | 6.4 | 1,773 |
| Example 5 | Compound (20 nm)/Compound 3-1 (10 nm) | 15,660 | 7.2 | 2,175 |
| Comparative Example 4 | Alq₃ (30 nm) | 10,070 | 6.0 | 1,678 |
| Comparative Example 5 | ET-12 | 13,850 | 6.8 | 2,036 |

From Table 2, the Example 3 employs the Compound 2-9 of the present invention as the electron transport layer, which achieves higher luminance and efficiency in the system of blue doping layer. The Examples 4 and 5 employs a double-layer structure for the electron transport layer with a difference that the electron transport materials in the two layers are different. View from the apparatuses, the Examples 4 and 5 still achieve higher luminance and efficiency. As compared with the apparatus comprising only the electron transport layer of Alq₃, the apparatuses of the Examples 3 to 5 are improved in all aspects of luminance, efficiency and current density. It shows that the compound of the present invention can be matched with other electron transport material (e.g., Alq$_3$) in order to achieve higher performance of the apparatus.

Example 6

Structure of apparatus: ITO/NPB (40 nm)/PADN (30 nm): 1% of C545 T/Compound 2-13 (30 nm)/Mg:Ag/Ag The apparatus is prepared according to the manner in the Example 3, except that the luminescent layer of the present Example is PADN and 2,3,6,7-tetrahydro-1,1,7,7-tetramethyl-1H,5H,11H-10-(2-benzothiazolyl)quinolizinocoumarin (C545T) with a thickness of 30 nm by double source codeposition wherein a ratio of C545T in PADN is controlled at 1% by rate, the Compound 2-13 with a thickness of 30 nm is deposited on the luminescent layer as the electron transport layer, Mg:Ag (10:1) with a thickness of 100 nm is deposited as the cathode by double source codeposition, and finally Ag with a thickness of 50 nm is coated as the protective layer.

Example 7

Structure of apparatus: ITO/NPB (40 nm)/PADN (30 nm): 1% of C545 T/Compound 2-13 (20 nm)/3-3 (10 nm)/Mg:Ag/Ag The apparatus is prepared according to the manner in the Example 6, except that the Compound 2-13 with a thickness of 20 nm and the Compound 3-3 with a thickness of 10 nm are successively deposited on the luminescent layer as the electron transport layer, Mg:Ag (10:1) with a thickness of 100 nm is deposited as the cathode by double source codeposition, and finally Ag with a thickness of 50 nm is coated as the protective layer.

Comparative Example 6

Structure of apparatus: ITO/NPB (40 nm)/PADN (30 nm): 1% of C545T/Alq$_3$ (30 nm)/Mg:Ag/Ag The apparatus is prepared according to the manner in the Example 6, except that Alq$_3$ with a thickness of 30 nm is deposited on the luminescent layer as the electron transport layer, Mg:Ag (10:1) with a thickness of 100 nm is deposited as the cathode by double source codeposition, and finally Ag with a thickness of 50 nm is coated as the protective layer.

Comparative Example 7

Structure of apparatus: ITO/NPB (40 nm)/PADN (30 nm): 1% of C545T/ET-11 (30 nm)/Mg:Ag/Ag The apparatus is prepared according to the manner in the Example 6, except that ET-11 with a thickness of 30 nm is deposited on the luminescent layer as the electron transport layer, Mg:Ag (10:1) with a thickness of 100 nm is deposited as the cathode by double source codeposition, and finally Ag with a thickness of 50 nm is coated as the protective layer.

TABLE 3

| Condition | | Luminance at 8 V (cd/m$^2$) | Efficiency at 8 V (cd/A) | Current density at 8 V (A/m$^2$) |
|---|---|---|---|---|
| Example 6 | Compound 2-13 (30 nm) | 25,780 | 19.6 | 1,316 |
| Example 7 | Compound 2-13 (20 nm)/ Compound 3-3 (10 nm) | 27,880 | 18.7 | 1,488 |
| Comparative Example 6 | Alq$_3$ (30 nm) | 20,350 | 11.8 | 1,725 |
| Comparative Example 7 | ET-11 | 23,890 | 17.9 | 1,334 |

From Table 3, the Examples 6 and 7 employs conventional green system of PADN:C545T for the luminescent layer, and its purpose is to verify the application prospect of the compound of the present invention as the electron transport layer in the green system. It can be seen from the comparison of the results of the apparatuses that the electron transport layer used whether in the double layer structure or in the single layer structure can efficiently reduce driving voltage and increase luminance and efficiency of the apparatus. The Examples 6 and 7 are greatly improved in all aspects of luminance, efficiency and current density as compared with the Comparative Example 6.

Example 8

Structure of apparatus: ITO/NPB (40 nm)/Alq$_3$ (50 nm)/Compound 2-21:CsCO$_3$ (20 nm, 10%)/Al (150 nm)

An ITO conductive glass substrate with a specific pattern etched is used as a substrate. The substrate is placed in deionized water containing a cleaning liquid at about 60° C. for ultrasonic cleaning. Then, the cleaned substrate is dried by using an infrared lamp and placed into a deposition chamber in which a hole inject layer, a hole transport layer, a luminescent layer, an electron transport layer, an electron inject layer and a cathode are successively deposited under a chamber pressure of less than $5.0 \times 10^{-3}$ Pa during deposition.

In the present Example, NPB with a thickness of 40 nm is firstly deposited on the ITO anode as the hole transport layer, 8-hydroxyquinolinato aluminum (Alq$_3$) with a thickness of 50 nm is successively deposited as the luminescent layer, the electron inject and transport functional layer with a thickness of 20 nm is deposited by codepositon wherein the doping concentration of the compound of CsCO$_3$ in the Compound 2-21 of the present invention is 10% (by weight), and finally Al with a thickness of 150 nm is deposited as the cathode.

Example 9

Structure of apparatus: ITO/NPB (40 nm)/Alq$_3$ (50 nm)/Compound 2-25:CsF (20 nm, 10%)/Al (150 nm)

The apparatus having the above structure is prepared according to the method in the Example 8, except that the Compound 2-25 of the present invention doped with 10% (by weight) of CsF is used as the electron inject and transport functional layer.

Example 10

Structure of apparatus: ITO/NPB (40 nm)/Alq$_3$ (50 nm)/Compound 2-28:KBH (20 nm, 10%)/Al (150 nm)

The apparatus having the above structure is prepared according to the method in the Example 8, except that the Compound 2-28 doped with 10% (by weight) of KBH is used as the electron inject and transport functional layer.

Example 11

Structure of apparatus: ITO/NPB (40 nm)/Alq$_3$ (20 nm)/Compound 2-18 (20 nm)/Compound 2-3:Li$_3$N (20 nm, 10%)/Al (150 nm)

The apparatus having the above structure is prepared according to the method in the Example 8, except that the luminescent layer is Alq$_3$ with a thickness of 30 nm, the Compound 2-18 with a thickness of 20 nm is firstly deposited thereon as a buffer layer of the apparatus, and then the Compound 2-3 doped with 10% (by weight) of Li$_3$N is used as the electron inject and transport functional layer.

Comparative Example 8

Structure of apparatus: ITO/NPB (40 nm)/Alq$_3$ (50 nm)/LiF (0.5 nm)/Al (150 nm)

The apparatus having the above structure is prepared according to the method in the Example 8, except that the apparatus contains no electron inject and transport functional layer of the present invention, and only employs the electron inject layer of LiF.

Comparative Example 9

Structure of apparatus: ITO/NPB (40 nm)/Alq$_3$ (50 nm)/Alq$_3$:KBH (20 nm, 10%)/Al (150 nm)

The apparatus having the above structure is prepared according to the method in the Example 8, except that the apparatus contains no electron inject and transport functional layer of the present invention, and only employs the electron inject layer of Alq$_3$:KBH.

Comparative Example 10

Structure of apparatus: ITO/NPB (40 nm)/Alq$_3$ (50 nm)/ET-12:Li$_3$N (20 nm, 10%)/Al (150 nm)

The apparatus having the above structure is prepared according to the method in the Example 8, except that the apparatus contains no electron inject and transport functional layer of the present invention, and only employs the electron inject layer of ET-12:Li$_3$N.

The performance data of the apparatuses in the above Examples are listed in following Table 4.

7.52V, and the efficiencies are up to 3.7 cd/A. The stabilities are compared by lives during which the luminance is decreased to 70%, and the lives are possibly 200 hours to 560 hours.

In the Example 11, one buffer layer which is the Compound 2-18 with a thickness of 20 nm is further disposed between the luminescent layer and the doped electron transport and inject layer. Adding the buffer layer can separate the luminescent layer from the inorganic dopant, prevent the inorganic dopant from diffusing into the luminescent layer, and thus increase the life of the apparatus more efficiently, the life being 558 hours when the luminance is decreased to 70%, which is significantly longer than the other Examples and the Comparative Examples.

The Comparative Example 8 is a conventional double layer apparatus of NPB/Alq$_3$/LiF/Al, and does not employ the doped structure of the present invention. Since the overall thickness of the organic layer in the apparatus is less than that in the Examples 1-4 (by 20 nm), the driving voltage is lower, 6.58V and the efficiency reaches 3.10 cd/A, but the life is only 120 hours. Besides, the Comparative Example 9 employ commonly used Alq3, and the Comparative Example 10 employs the material of ET-12. Since the electron mobilities of Alq$_3$ and BAlq is less than that of the organic material of the present invention, After the dopant is mixed therewith, the Comparative Examples show higher driving voltages and lower efficiencies. The lives of the Comparative Examples 9 and 10 are less than that of the Examples by 20% or more, although they are improved relative to the Comparative Example 8, which is related to lower glass transition temperatures of Alq$_3$ and ET-12.

Example 12

Structure of apparatus: ITO/m-MTDATA:F$_4$-TCNQ (150 nm, 2%)/NPB (20 nm)/MADN:TBPe (30 nm, 5 %)/Alq$_3$ (10 nm)/Compound 2-33: CsF (10 nm, 5%)/Al (150 nm)

The apparatus having the above structure is prepared according to the method in the Example 1. The hole inject layer is deposited on the ITO anode surface, the hole inject layer being m-MTDATA doped with 2% of F$_4$-TCNQ with a thickness of 150 nm. NPB with a thickness of 20 nm is deposited thereon as the hole transport layer. The luminescent layer is a blue host of 2-methyl-9,10-di(2-naphthyl)-anthracene (MADN) doped with 5% of a blue dye of 2,5,8,11-tetratertbutylperylene (TBPe) and has a thickness of 30 nm.

TABLE 4

| | Structure of apparatus | Luminance cd/m$^2$ | Voltage V | Current density A/m$^2$ | Current efficiency cd/A | T$_{70\%}$(h) @2000 cd/m$^2$ |
|---|---|---|---|---|---|---|
| Example 8 | Compound 2-21:CsCO$_3$ (20 nm, 10%)/Al | 2000 | 6.78 | 539.94 | 3.70 | 358 |
| Example 9 | Compound 2-25:CsF (20 nm, 10%)/Al | 2000 | 6.86 | 628.54 | 3.18 | 216 |
| Example 10 | Compound 2-28:KBH (20 nm, 10%)/Al | 2000 | 7.52 | 554.56 | 3.61 | 455 |
| Example 11 | Compound 2-18(20 nm)/Compound 2-3:Li$_3$N (20 nm, 10%)/Al | 2000 | 6.48 | 662.71 | 3.02 | 558 |
| Comparative Example 8 | LiF(0.5nnm)/Al(150 nm) | 2000 | 6.58 | 645.16 | 3.10 | 120 |
| Comparative Example 9 | Alq$_3$:KBH(20 nm, 10%)/Al(150 nm) | 2000 | 7.55 | 692.04 | 2.89 | 169 |
| Comparative Example 10 | ET-12:Li$_3$N(20 nm, 10%)/Al(150 nm) | 2000 | 7.21 | 653.59 | 3.06 | 187 |

From Table 4, the Examples 8 to 11 are typical double layer apparatuses of NPB/Alq$_3$ and employ the Compound 2-21, the Compound 2-25 and the Compound 2-28 to be mixed with different dopants. Their driving voltages, efficiencies and stabilities are compared. At luminance of 2000 cd/m$^2$, the driving voltages are distributed in the range of 6.48V to The buffer layer between the luminescent layer and the electron transport and inject layer has a thickness of 10 nm and the deposition material thereof is $Alq_3$. The electron inject and transport functional layer is prepared using the Compound 2-33 and CsF by codeposition and has a thickness of 10 nm, and the doping concentration of CsF is 5%. Finally, Al metal with a thickness of 150 nm is deposited as the cathode.

Example 13

Structure of apparatus: ITO/m-MTDATA:$F_4$-TCNQ (150 nm, 2%)/NPB (20 nm)/MADN:TBPe (30 nm, 5%)/BCP (2 nm)/Compound 2-33:$Li_3N$ (10 nm, 25%)/Al (150 nm)

The apparatus having the above structure is prepared according to the method in the Example 12, except that the buffer layer between the luminescent layer and the electron transport and inject layer has a thickness of 2 nm and the deposition material thereof is 2,9-dimethyl-4,7-diphenyl-1,10-phenanthroline (BCP), and the electron inject and transport functional layer is prepared using the Compound 2-33 and $Li_3N$ by codeposition and has a thickness of 10 nm, and the doping concentration of $Li_3N$ is 25%.

Example 14

Structure of apparatus: ITO/m-MTDATA:$F_4$-TCNQ (150 nm, 2%)/NPB (20 nm)/MADN:TBPe (30 nm, 5%)/PBD (20 nm)/Compound 2-33:LiF (10 nm, 50%)/Al (150 nm)

The apparatus having the above structure is prepared according to the method in the Example 12, except that the buffer layer between the luminescent layer and the electron transport and inject layer has a thickness of 20 nm and the deposition material thereof is 2-(4-diphenyl)-5-(4-tertbutylphenyl)-1,3,4-oxadiazole (PBD), and the electron inject and transport functional layer is prepared using the Compound 2-33 and LiF by codeposition and has a thickness of 10 nm, and the doping concentration of LiF is 50%.

Comparative Example 11

Structure of apparatus: ITO/m-MTDATA:$F_4$-TCNQ (150 nm, 2%)/NPB (20 nm)/MADN:TBPe (30 nm, 5%)/$Alq_3$ (20 nm)/LiF (0.5 nm)/Al (150 nm)

The apparatus having the above structure is prepared according to the method in the Example 12, except that there is no doped electron transport and inject layer, and instead, $Alq_3$ with a thickness of 20 nm is directly deposited on the luminescent layer as the electron transport layer, and finally LiF with a thickness of 0.5 nm and Al with a thickness of 150 nm are respectively deposited as the electron inject layer and the cathode.

Comparative Example 12

Structure of apparatus: ITO/m-MTDATA:$F_4$-TCNQ (150 nm, 2%)/NPB (20 nm)/MADN:TBPe (30 nm, 5%)/Compound 2-33 (20 nm)/LiF (0.5 nm)/Al (150 nm)

The apparatus having the above structure is prepared according to the method in the Example 12, except that there is no doped electron transport and inject layer, and instead, the Compound 2-33 with a thickness of 20 nm is directly deposited on the luminescent layer as the electron transport layer, and finally LiF with a thickness of 0.5 nm and Al with a thickness of 150 nm are respectively deposited as the electron inject layer and the cathode.

The performance data of the apparatuses in the above Examples 12 to 14 and the Comparative Examples 11 and 12 are listed in following Table 5.

| | Structure of apparatus | Luminance $cd/m^2$ | Voltage V | Current density $A/m^2$ | Current efficiency cd/A | x(5 V) | y(5 V) |
|---|---|---|---|---|---|---|---|
| Example 12 | $Alq_3$(10 nm)/Compound 2-33:CsF(10 nm, 5%) | 5000 | 8.06 | 722.07 | 6.92 | 0.1434 | 0.1901 |
| Example 13 | BCP(2 nm)/Compound 2-33:$Li_3N$(10 nm, 25%) | 5000 | 8.52 | 762.84 | 6.55 | 0.1419 | 0.1892 |
| Example 14 | PBD(20 nm)/Compound 2-33:LiF(10 nm, 50%) | 5000 | 8.35 | 813.71 | 6.14 | 0.1415 | 0.1874 |
| Comparative Example 11 | $Alq_3$(20 nm)/LiF/Al | 5000 | 9.85 | 915.39 | 5.46 | 0.1417 | 0.1879 |
| Comparative Example 12 | Compound 2-33 (20 nm)/LiF/Al | 5000 | 5.90 | 751.57 | 6.65 | 0.1417 | 0.1810 |

The Examples 12 to 14 employ the Compound 2-33 doped with the dopant in different ratios (the concentration being 5% to 50%), while the buffer layer employs different materials having electron transport property, and thus the obtained apparatuses have better performance. As compared with the Comparative Example 11, they have lower driving voltages wherein the voltage is reduced by 1.8V at best. The efficiencies of the apparatuses wherein the Compound 2-33 is doped are also higher, and are increased by 0.5 to 1.5 cd/A as compared with 5.46 cd/A in the Comparative Example 11 which increases by 27% at best. Meanwhile, from the comparison of the stabilities, after the Compound 2-33 is doped, the apparatuses all have prolonged half lives (initial luminance of 5000 $cd/m^2$), which increased by 50% or more relative to that of the Comparative Example 11. The use of the buffer layer separates the inorganic dopant from the luminescent layer, which avoids luminescent quenching phenomenon and is beneficial for improvement of the stability of the apparatus.

In addition, the Comparative Example 12 employs undoped Compound 2-33. As compared with the Examples 12 to 14, the Comparative Example 12 has very low driving voltage which is only 5.9V due to lack of $Alq_3$ having lower mobility. However, the life of the Comparative Example 12 is less than those of the Examples 12 to 14 due to undoping.

It can be seen that by matching ETL and a dopant material and designing reasonable doping ratio and structure of apparatus, a balance point can be find among the driving voltage, the efficiency and the stability, thereby achieving an apparatus having optimal performance and higher practicability, and improving performance of OLED product.

Example 15

Structure of apparatus: ITO/NPB (40 nm)/Alq$_3$ (30 nm)/Compound 2-5 (20 nm)/Compound 2-5: Li$_3$N (10 nm, 10%)/V$_2$O$_5$ (10 nm)/NPB (40 nm)/Alq$_3$ (30 nm)/Compound 2-5 (20 nm)/LiF (0.5 nm)/Al (150 nm)

An ITO conductive glass substrate with a specific pattern etched is used as a substrate. The substrate is placed in deionized water containing a cleaning liquid at about 60° C. for ultrasonic cleaning. Then, the cleaned substrate is dried by using an infrared lamp and placed into a deposition chamber in which each functional layer is successively deposited under a chamber pressure of less than 5.0×10$^{-3}$ Pa during deposition.

In the present Example, a first luminescent unit is firstly prepared on the ITO anode. NPB with a thickness of 40 nm is deposited as the hole transport layer, Alq$_3$ with a thickness of 30 nm is then deposited thereon as the luminescent layer, the electron transport layer with a thickness of 20 nm is deposited and employs the Compound 2-5 of the present invention. Then, connection layers are prepared on the first luminescent unit. An N-type connection layer is deposited by codepositing the Compound 2-5 and 10% by weight of Li$_3$N to a thickness of 10 nm, and a P-type connection layer is obtained by depositing V$_2$O$_5$ to a thickness of 10 nm. Subsequently, a second luminescent unit is prepared on the connection layers by deposition, and the structure and the deposition order of the second luminescent unit are the same as those of the first luminescent unit. Finally, the electron inject layer of LiF with a thickness of 0.5 nm is deposited by thermal deposition, and the cathode metal layer of Al with a thickness of 150 nm is coated thereon.

Example 16

Structure of apparatus: ITO/NPB (40 nm)/Alq$_3$ (30 nm)/Compound 2-35 (20 nm)/Compound 2-35:Li$_3$N (10 nm, 10%)/V$_2$O$_5$ (10 nm)/NPB (40 nm)/Alq$_3$ (30 nm)/Compound 2-35 (20 nm)/LiF (0.5 nm)/Al (150 nm)

The apparatus having the above structure is prepared according to the manner in the Example 15, except that the material used in the electron transport layer and in the N-type layer in the connection layers is changed to the Compound 2-35.

Example 17

Structure of apparatus: ITO/NPB (40 nm)/Alq$_3$ (30 nm)/Compound 3-3 (20 nm)/Compound 2-13:Li$_3$N (10 nm, 10%)/V$_2$O$_5$ (10 nm)/NPB (40 nm)/Alq$_3$ (30 nm)/Compound 3-3 (20 nm)/LiF (0.5 nm)/Al (150 nm)

The apparatus having the above structure is prepared according to the manner in the Example 15, except that the material used in the electron transport layer is changed to the Compound 3-3 and the material used in the N-type layer in the connection layers is changed to the Compound 2-13.

Comparative Example 8

Structure of apparatus: ITO/NPB (40 nm)/Alq$_3$ (30 nm)/Alq$_3$ (20 nm)/LiF (0.5 nm)/Al (150 nm)

The preparation method is described as above.

Comparative Example 13

Structure of apparatus: ITO/NPB (40 nm)/Alq$_3$ (30 nm)/Alq$_3$ (20 nm)/Alq$_3$:Li$_3$N (10 nm, 10%)/V$_2$O$_5$ (10 nm)/NPB (40 nm)/Alq$_3$ (30 nm)/Alq$_3$ (20 nm)/LiF (0.5 nm)/Al (150 nm)

The apparatus having the above structure is prepared according to the manner in the Example 15, except that the material used in the electron transport layer and in the N-type layer in the connection layers is changed to Alq$_3$.

|  | Voltage at 2000 cd/m$^2$ V | Current efficiency at 2000 cd/m$^2$ cd/A | Lumen efficiency at 2000 cd/m$^2$ lm/W |
|---|---|---|---|
| Example 15 | 13.0 | 6.1 | 1.2 |
| Example 16 | 13.2 | 5.8 | 1.1 |
| Example 17 | 12.8 | 6.4 | 1.2 |
| Comparative Example 8 | 6.6 | 3.1 | 1.2 |
| Comparative Example 13 | 13.8 | 5.3 | 1.1 |

The Comparative Example 8 is an apparatus having a single luminescent unit, and employs Alq$_3$ with a thickness of 20 nm as the electron transport layer. The Examples 15 to 17 and the Comparative Example 13 are apparatuses wherein two luminescent units are stacked, and their difference lies that the Comparative Example employs Alq$_3$ as the electron transport layer and the N-type layer in the connection layers, while the Examples 15 to 17 employ the compounds of the present invention.

It can be seen from the comparison of the performance in the above table that the current efficiency of the apparatus employing the structure wherein two luminescent units are stacked is increased about 100% as compared with the apparatus comprising the single luminescent unit. The compounds 2-5, 2-35 and 2-13 of the present invention not only are used as the electron transport layer, but also are used as the host material in the N-type connection of the N/P connection layers. Moreover, the current efficiencies of the Examples 15 to 17 are also obviously higher than that of the Comparative Example 13. By comparing the Examples and the Comparative Example 8, the driving voltages of the Examples 15 to 17 are less than twice of the driving voltage of the Comparative Example 8, although the Examples 15 to 17 have two luminescent units. It can be seen that the compound of the present invention as the N-type layer in the connection layers has more efficient electron generating and inject ability and can significantly decrease driving voltage and increase efficiency.

Example 18

Structure of apparatus: ITO/HAT (5 nm)/NPB (20 nm)/Alq$_3$:C545T (30 nm, 1%)/Alq$_3$ (20 nm)/Compound 2-28:Li$_3$N (20 nm, 5%)/MoO$_3$ (15 nm)/NPB (20 nm)/Alq$_3$:C545T (30 nm, 1%)/Alq$_3$ (20 nm)/LiF (0.5 nm)/Al (150 nm)

The apparatus having the above structure is prepared according to the manner in the Example 15, except that the hole inject layer of HAT with a thickness of 5 nm is firstly deposited on ITO, the hole transport layer of NPB has a thickness of 20 nm, the luminescent layer is a system in which Alq$_3$ is doped with C545T and has a thickness of 30 nm, the concentration of the green dye is 1%, the electron transport layer is changed to Alq$_3$, the N-type layer in the connection layers is the Compound 2-28 doped with 5% of Li$_3$N and has a thickness of 20 nm, and the P-type connection layer is MoO$_3$ and has a thickness of 15 nm.

Example 19

Structure of apparatus: ITO/HAT (5 nm)/NPB (20 nm)/Alq$_3$:C545T (30 nm, 1%)/Alq$_3$ (20 nm)/Compound 2-28:

Li$_3$N (15 nm, 20%)/m-MTDATA:F$_4$-TCNQ (20 nm, 2%)/NPB (20 nm)/Alq$_3$:C545T (30 nm, 1%)/Alq$_3$ (20 nm)/LiF (0.5 nm)/Al (150 nm)

The apparatus having the above structure is prepared according to the manner in the Example 18, except that the N-type layer in the connection layers has a thickness of 15 nm and a doping ratio of 20%, and the P-type layer is m-MTDATA doped with 2% of F$_4$-TCNQ and has a thickness of 20 nm.

Example 20

Structure of apparatus: ITO/HAT (5 nm)/NPB (20 nm)/Alq$_3$:C545T (30 nm, 1%)/Alq$_3$ (20 nm)/Compound 2-28: Li$_3$N (5 nm, 10%)/HAT (5 nm)/NPB (20 nm)/Alq$_3$:C545T (30 nm, 1%)/Alq$_3$ (20 nm)/LiF (0.5 nm)/Al (150 nm)

The apparatus having the above structure is prepared according to the manner in the Example 18, except that the N-type layer in the connection layers has a thickness of 5 nm and a doping ratio of 10%, and the P-type layer is HAT (hexanitrile hexaazatriphenylene) and has a thickness of 5 nm.

Example 21

Structure of apparatus: ITO/HAT (5 nm)/NPB (20 nm)/Alq$_3$:C545T (30 nm, 1%)/Alq$_3$ (20 nm)/Compound 2-28: 70% of Li$_3$N (5 nm, 10%)/HAT (5 nm)/NPB (20 nm)/Alq$_3$:C545T (30 nm, 1%)/Alq$_3$ (20 nm)/LiF (0.5 nm)/Al (150 nm)

The apparatus having the above structure is prepared according to the manner in the Example 20, except that the doping ratio of Li$_3$N in the N-type layer of the connection layers is 70%.

Comparative Example 14

Structure of apparatus: ITO/HAT (5 nm)/NPB (20 nm)/Alq$_3$:C545T (30 nm, 1%)/Alq$_3$ (20 nm)/LiF (0.5 nm)/Al (150 nm)

The apparatus having the above structure is prepared according to the manner in the Example 18, except that the apparatus comprises only one luminescent unit and no connection layer.

Comparative Example 15

Structure of apparatus: ITO/HAT (5 nm)/NPB (20 nm)/Alq$_3$:C545T (30 nm, 1%)/Alq$_3$ (20 nm)/Alq$_3$: Li (10 nm, 10%)/HAT (10 nm)/NPB (20 nm)/Alq$_3$:C545T (30 nm, 1%)/Alq$_3$ (20 nm)/LiF (0.5 nm)/Al (150 nm)

The apparatus having the above structure is prepared according to the manner in the Example 18, except that the N-type layer in the connection layers is Alq$_3$ doped with 10% of Li and has a thickness of 10 nm, and the P-type layer is HAT with a thickness of 10 nm.

Comparative Example 16

Structure of apparatus: ITO/HAT (5 nm)/NPB (20 nm)/Alq$_3$:C545T (30 nm, 1%)/Alq$_3$ (20 nm)/ET-11:Li (10 nm, 10%)/HAT (10 nm)/NPB (20 nm)/Alq$_3$:C545T (30 nm, 1%)/Alq$_3$ (20 nm)/LiF (0.5 nm)/Al (150 nm)

The apparatus having the above structure is prepared according to the manner in the Example 18, except that the N-type layer in the connection layers is ET-11 doped with 10% of Li and has a thickness of 10 nm, and the P-type layer is HAT with a thickness of 10 nm.

| | Voltage at 1000 cd/m$^2$ V | Current efficiency at 1000 cd/m$^2$ cd/A | Lumen efficiency at 1000 cd/m$^2$ lm/W |
|---|---|---|---|
| Example 18 | 8.0 | 15.0 | 5.89 |
| Example 19 | 8.5 | 14.8 | 5.47 |
| Example 20 | 7.5 | 16.2 | 6.78 |
| Example 21 | 9.2 | 14.5 | 4.95 |
| Comparative Example 14 | 4.2 | 8.0 | 5.9 |
| Comparative Example 15 | 8.9 | 14.6 | 5.16 |
| Comparative Example 16 | 8.8 | 14.8 | 5.21 |

The Comparative Example 14 is an apparatus having a single luminescent unit. The Comparative Example 15 and the Examples 18 to 21 are apparatuses wherein two luminescent units are stacked, and their difference lies that the material of the N-type connection layer in the Comparative Example 15 employs Alq$_3$, while the material of the N-type connection layer in the Examples 18 to 21 employ the Compound 2-28 of the present invention and matches with different P-type connection layers. The N-type connection layer in the Comparative Example 16 employs ET-11, and the driving voltage of the apparatus is slightly higher than that of the Examples and the efficiency is slightly lower. It demonstrates that the compound of the present invention has better transport property than ET-11.

It can be seen from the comparison of the performance in the above table that the connection layer of 2-28: 10% of Li$_3$N/HAT is the preferable structure in this series. The Example 20 are significantly improved in terms of current efficiency and lumen efficiency as compared with the other apparatuses. As compared with the Comparative Example 14 comprising the single luminescent unit, the Example 20 has a driving voltage less than twice of the voltage of the Comparative Example. It shows that the connection layer in the Example 20 has optimal carrier generating and inject property and increases efficiency of the stacked apparatus.

What is claimed is:
1. An organic material represented by following Formula 1:

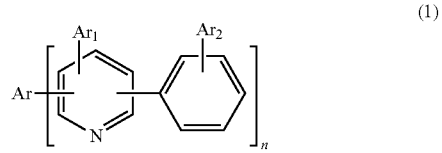

wherein Ar$_1$ is hydrogen, and Ar$_2$ is selected from the group consisting of hydrogen, C6-C24 aryl, and C6-C24 heterocyclic aryl, and n is an integer selected from 2 and 3, and wherein Ar has a chemical structure selected from:

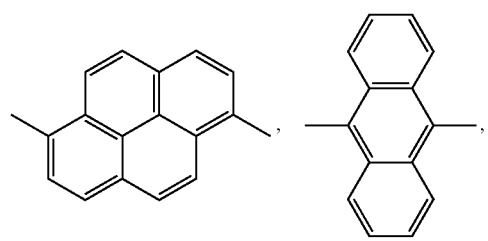

-continued
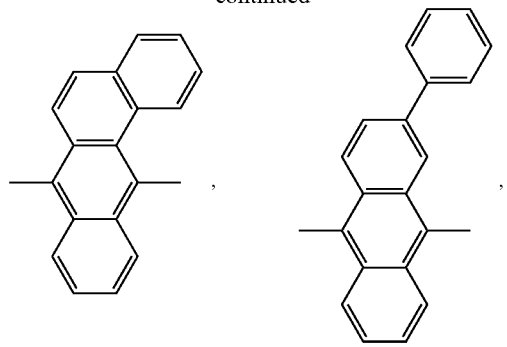
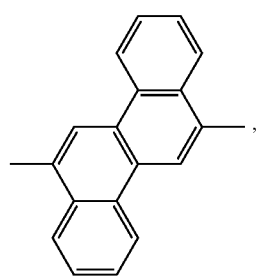
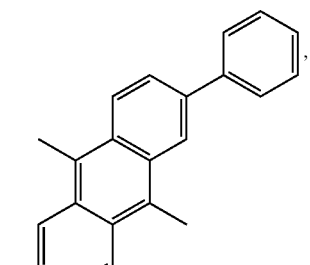
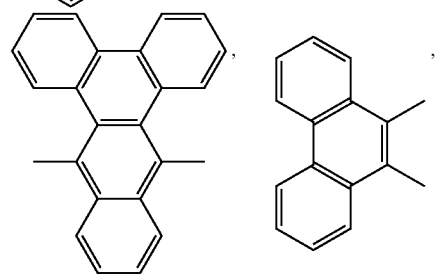
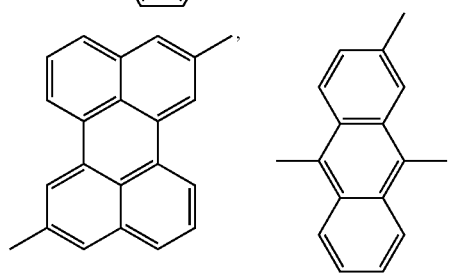
-continued
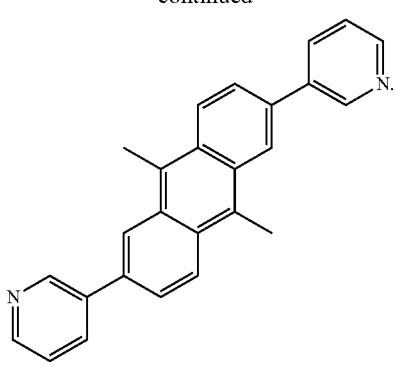
2. The organic material of claim 1, wherein Formula 1 is one of following Formulae 2 to 7:
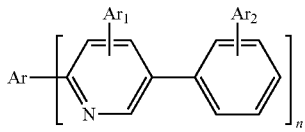 (2)
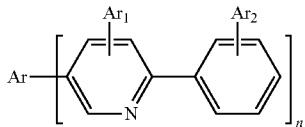 (3)
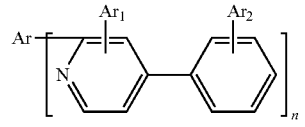 (4)
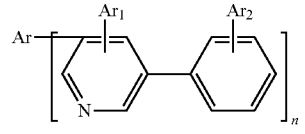 (5)
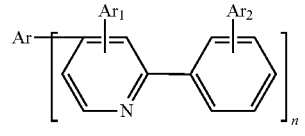 (6)
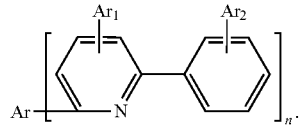 (7)
3. The organic material of claim 1, wherein the group connected to Ar is selected from:
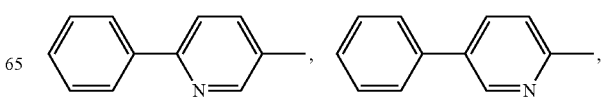

-continued
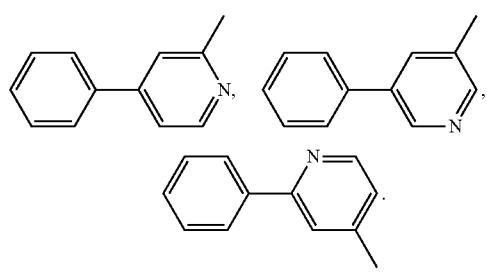
4. The organic material of claim 1, wherein the organic material has a chemical structure selected from:
2-1
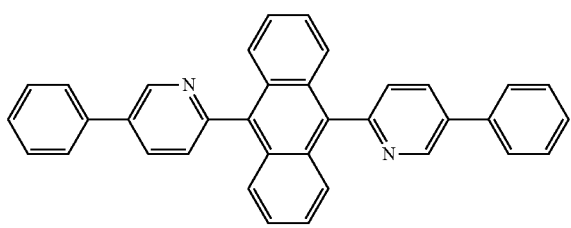
2-3
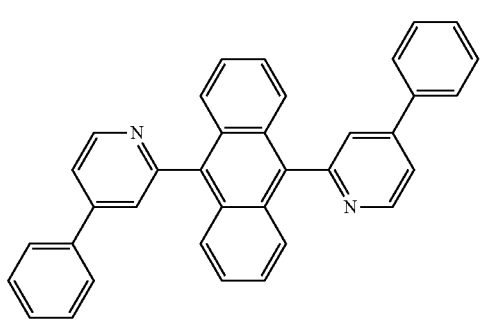
2-5
2-7
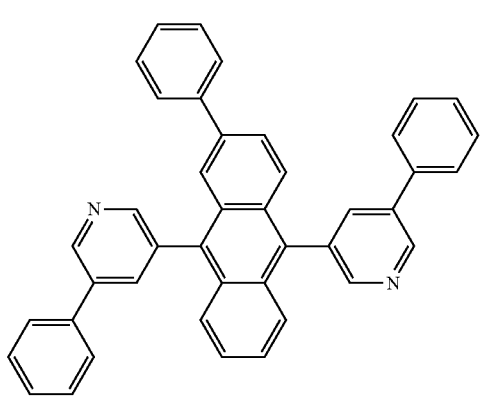
-continued
2-9
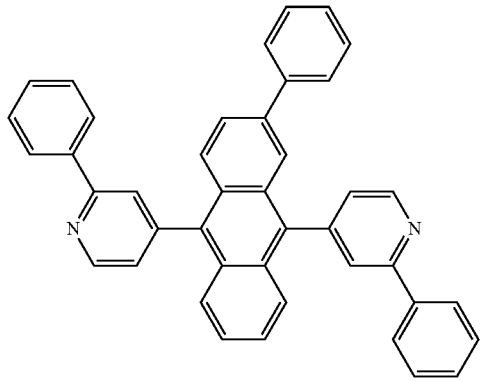
2-11
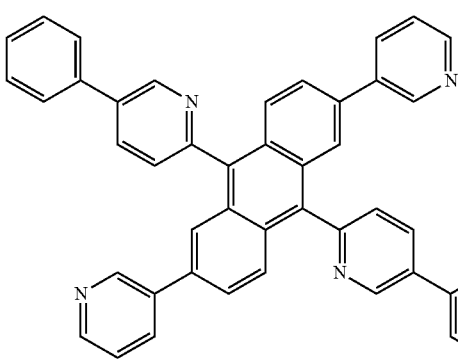
2-13
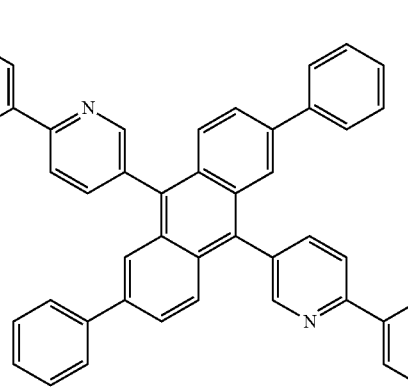
2-15
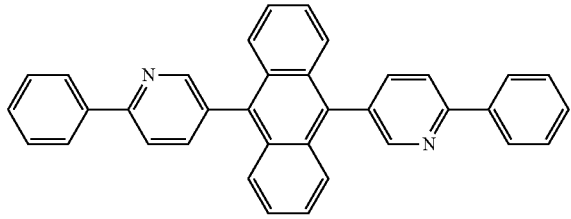

2-18
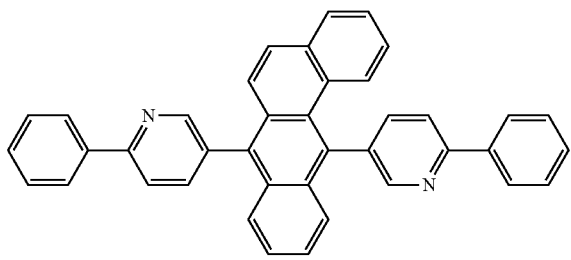
2-19
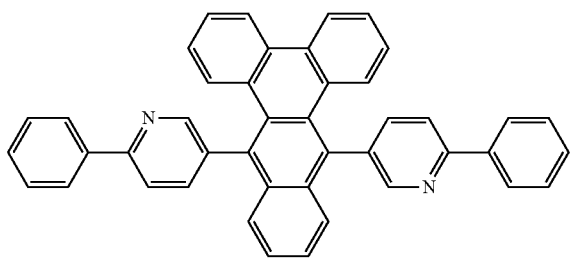
2-21
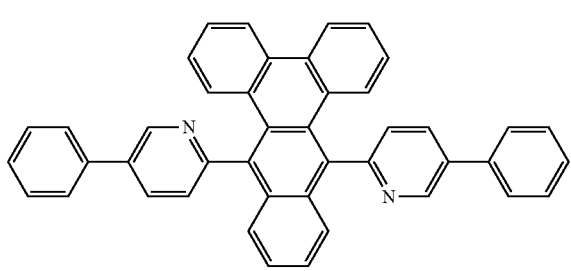
2-23
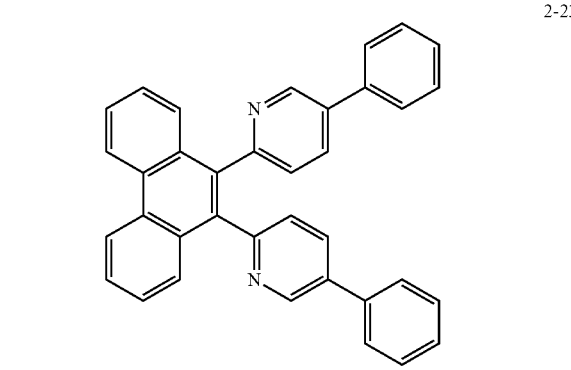
2-25
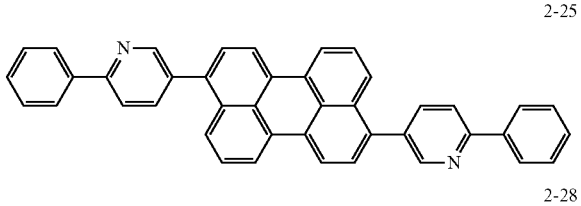
2-28
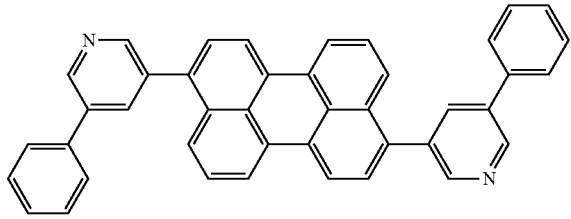
2-31
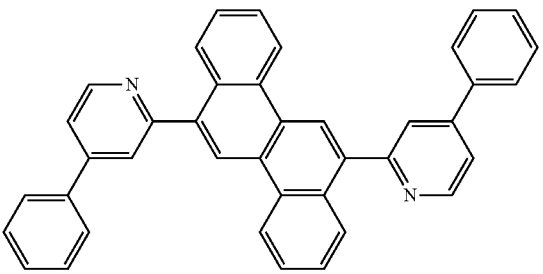
2-33
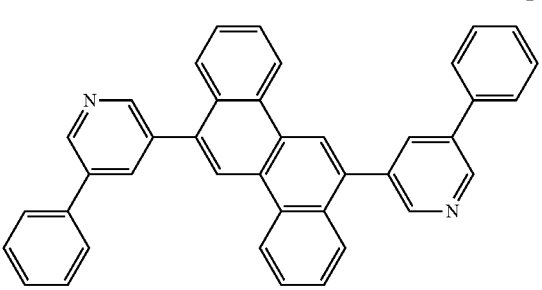
2-35
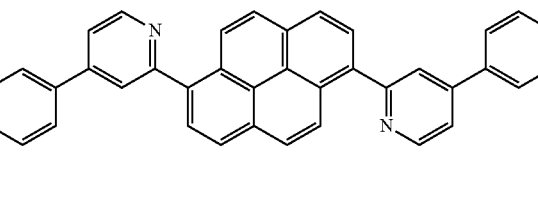
2-37
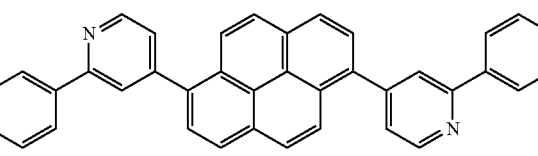
3-1
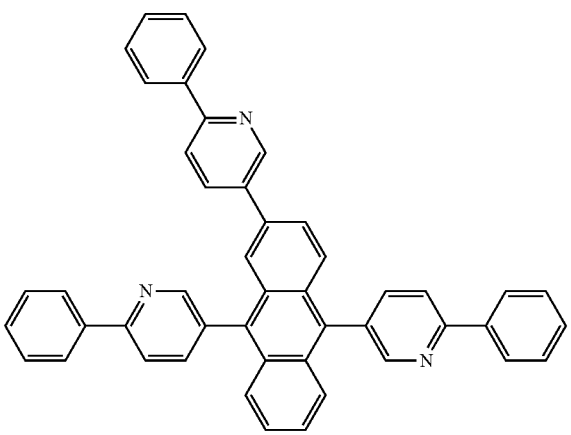

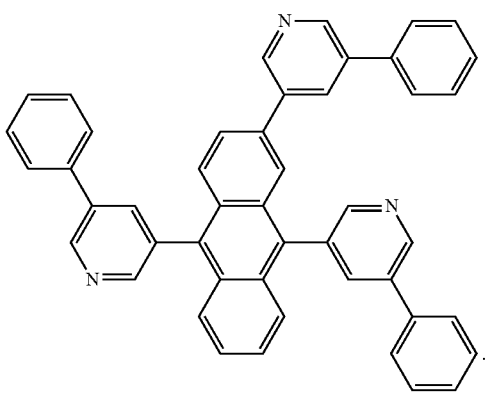

5. An organic electroluminescent apparatus comprising the organic material of claim 1 as an electron transport material.

6. The organic electroluminescent apparatus of claim 5, wherein Formula 1 is one of following Formulae 2 to 7:

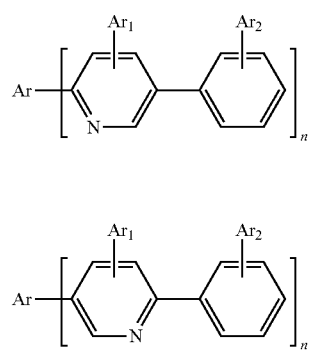 (2)

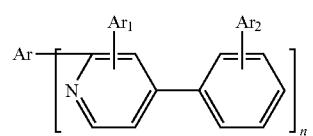 (3)

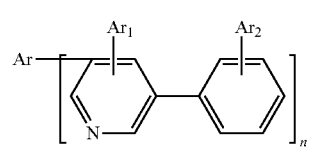 (4)

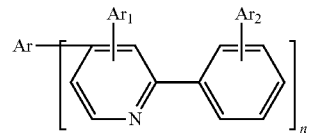 (5)

(6)

(7)

7. The electroluminescent apparatus of claim 5, wherein the group connected to Ar is selected from:

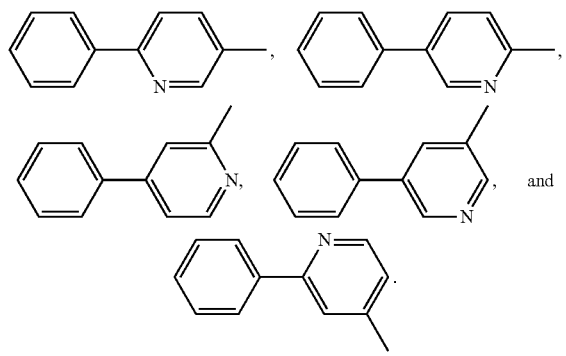

8. The electroluminescent apparatus of claim 5, wherein the organic material has a chemical structure selected from:

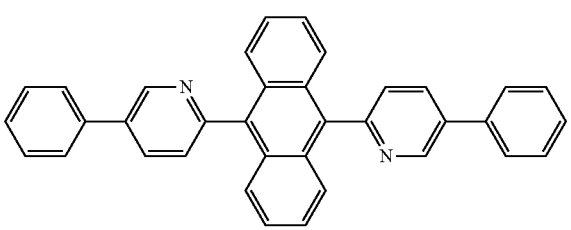

2-1

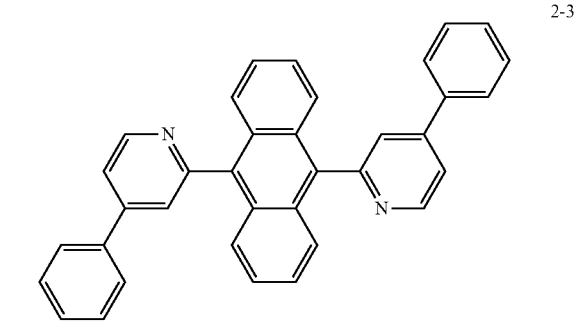

2-3

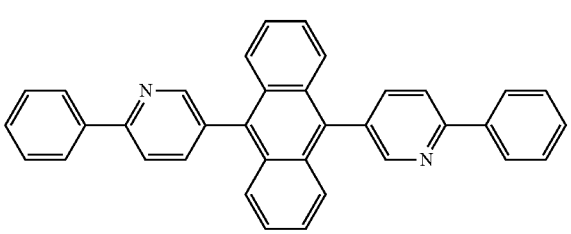

2-5

2-7
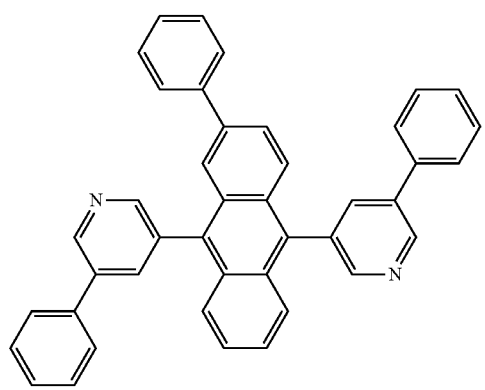
2-15
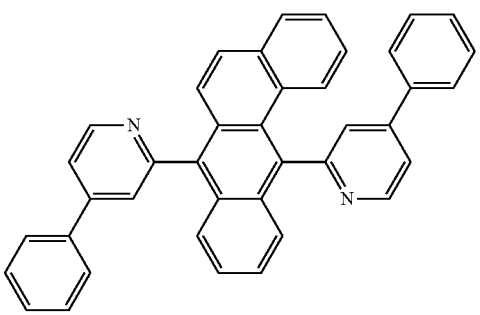
2-9
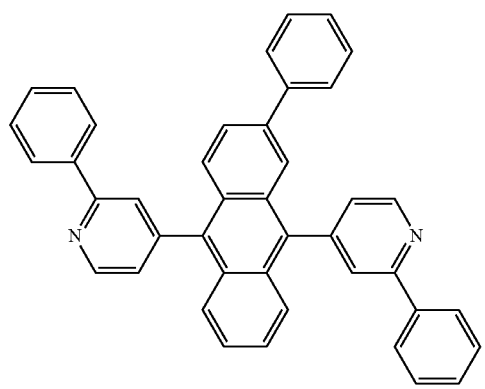
2-18
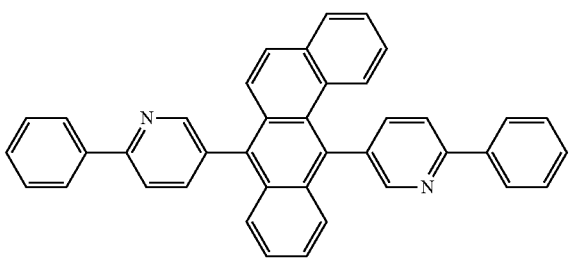
2-11
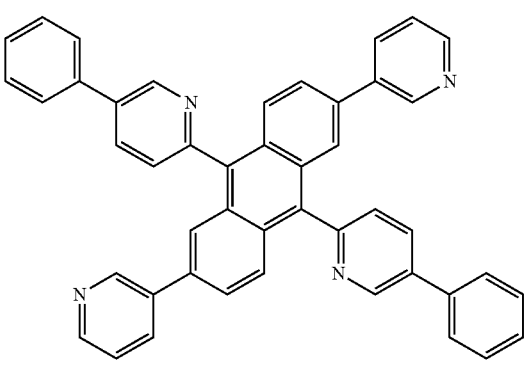
2-19
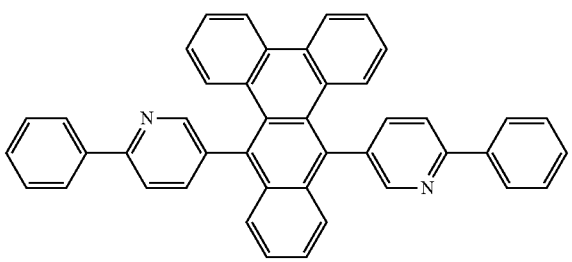
2-21
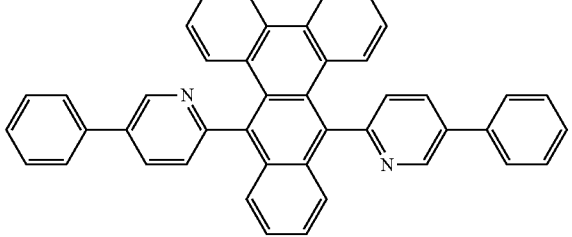
2-13
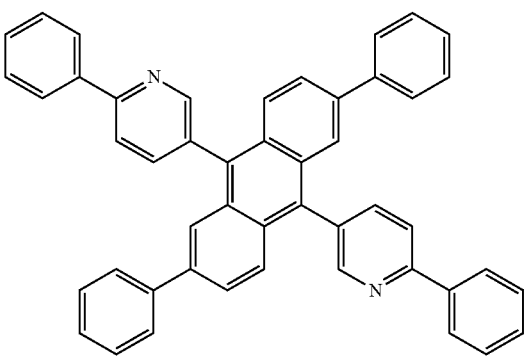
2-23
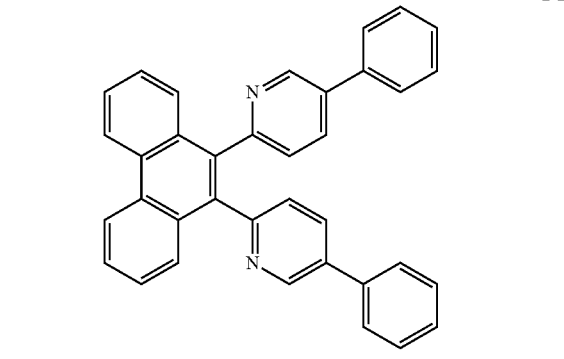

2-25
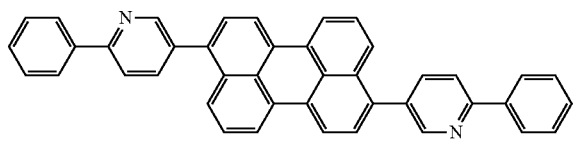
2-28
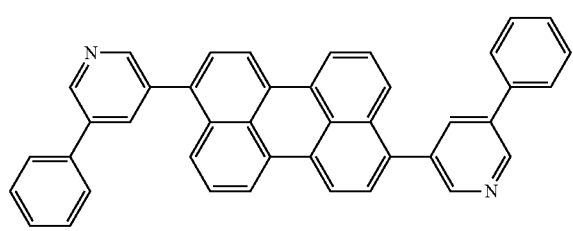
2-31
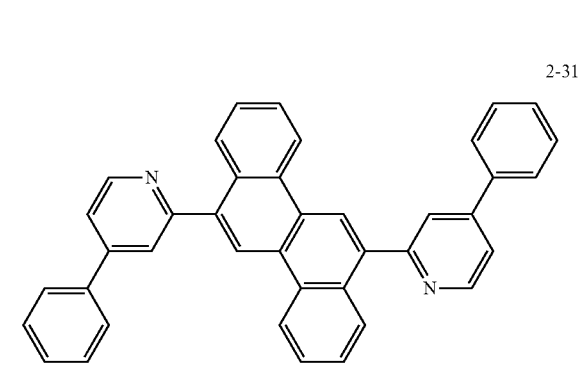
2-33
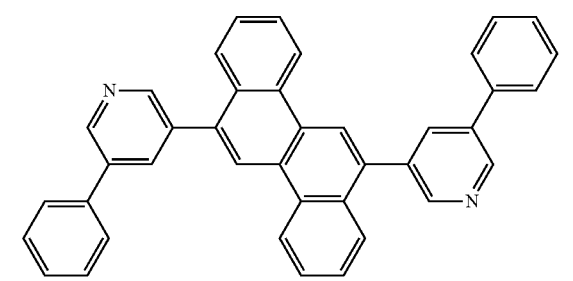
2-35
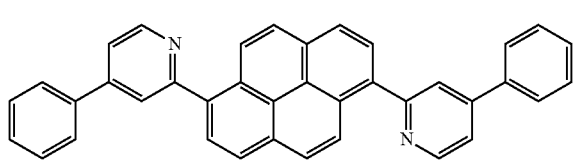
2-37
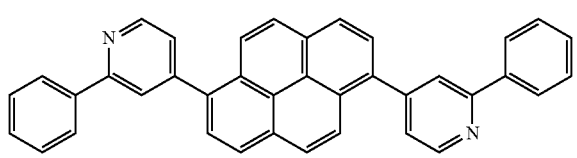
3-1
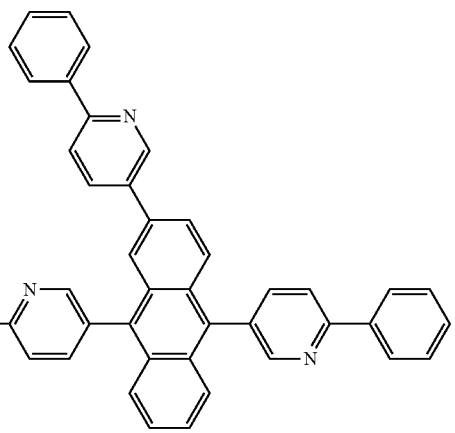
3-3
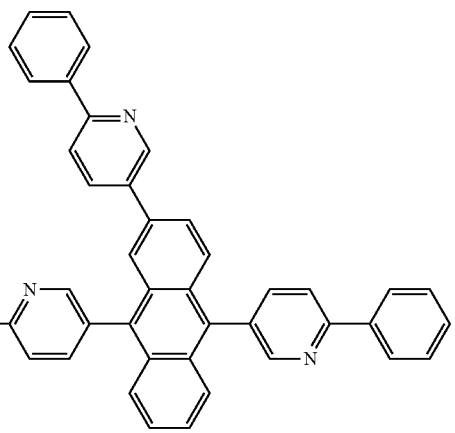
9. An organic electroluminescent apparatus comprising a pair of electrodes and an organic luminescent medium disposed between the pair of electrodes, the organic luminescent medium comprising the organic material of claim 1.
10. The organic electroluminescent apparatus of claim 9, wherein the Formula 1 is one of following Formulae 2 to 7:
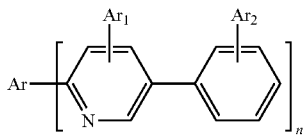
(2)
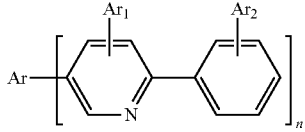
(3)
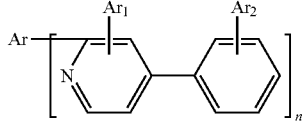
(4)

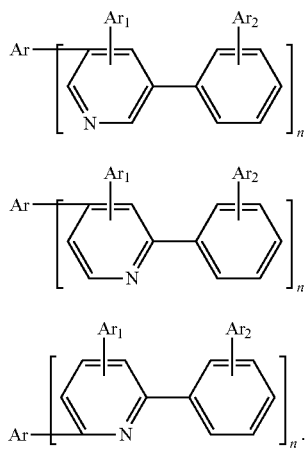
11. The organic electroluminescent apparatus of claim 9, wherein the group connected to Ar is selected from:
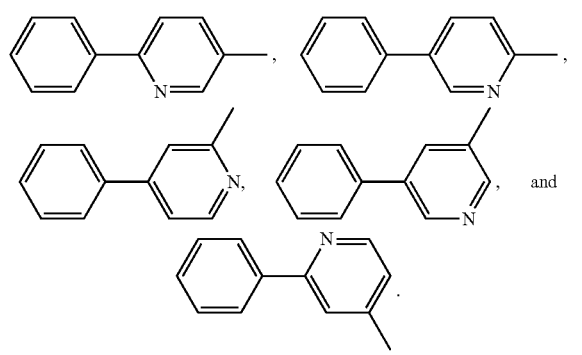
12. The organic electroluminescent apparatus of claim 9, wherein the organic material is represented by following structural formulae:
2-1
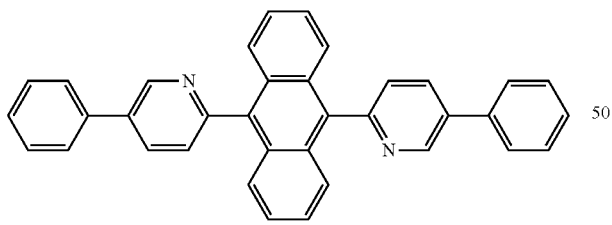
2-3
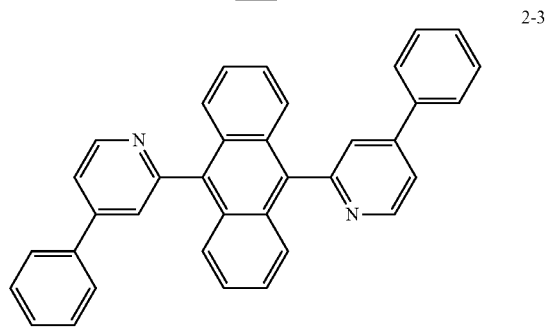
2-5
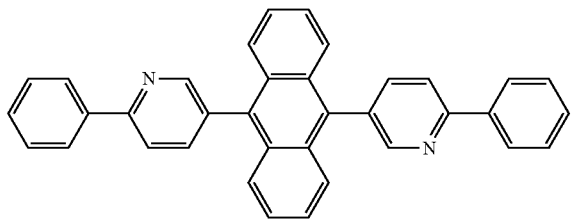
2-7
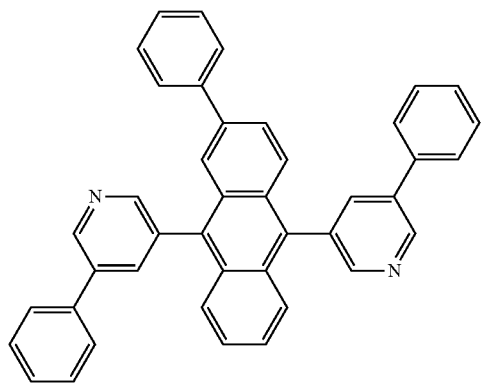
2-9
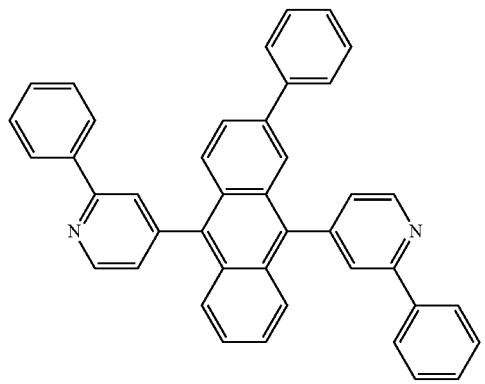
2-11
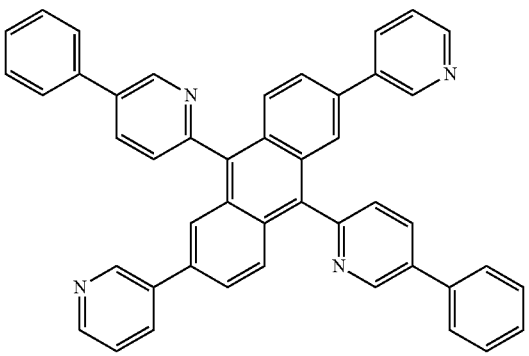

2-13
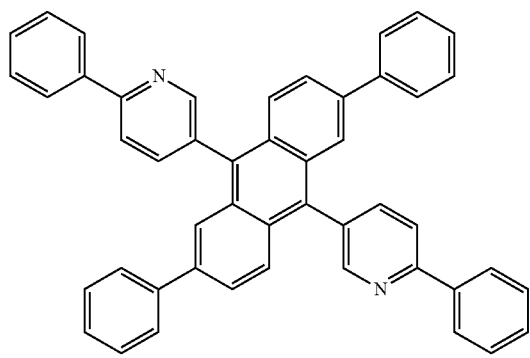
2-15
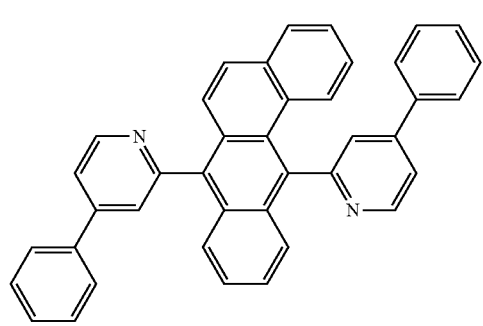
2-18
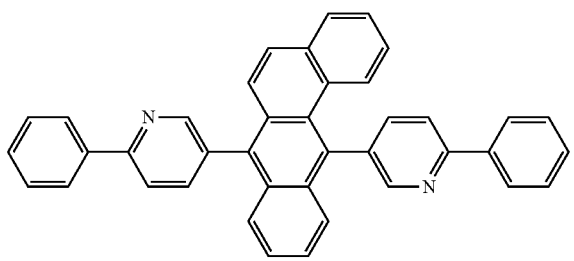
2-19
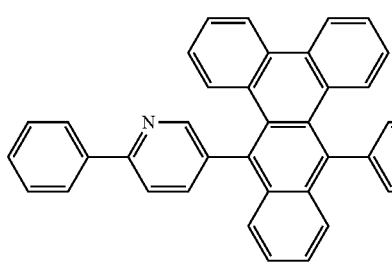
2-21
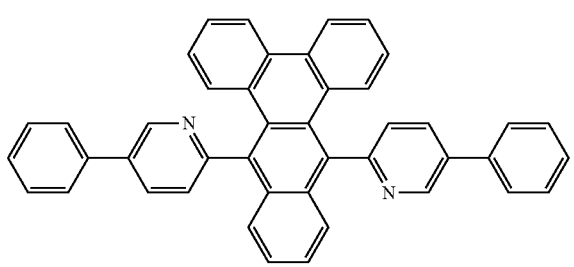
2-23
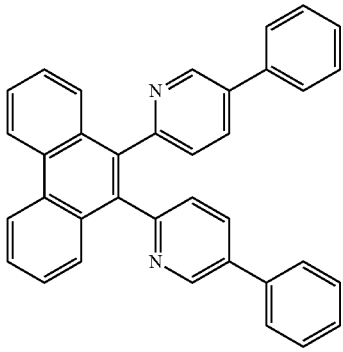
2-25
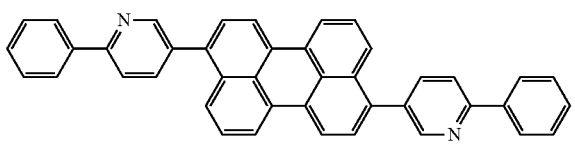
2-28
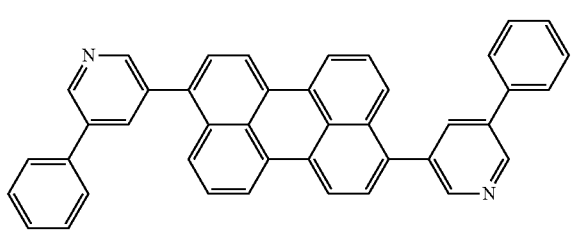
2-31
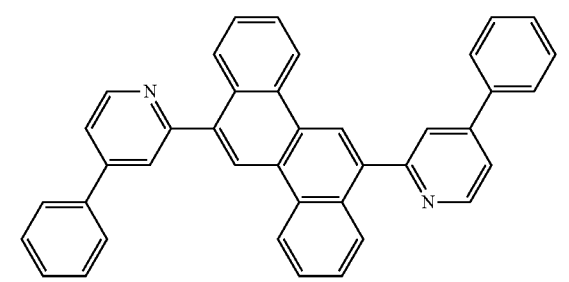
2-33
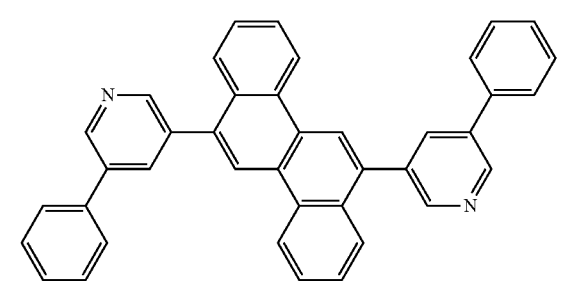
2-35
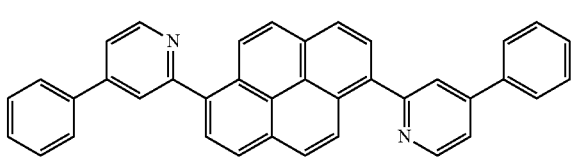

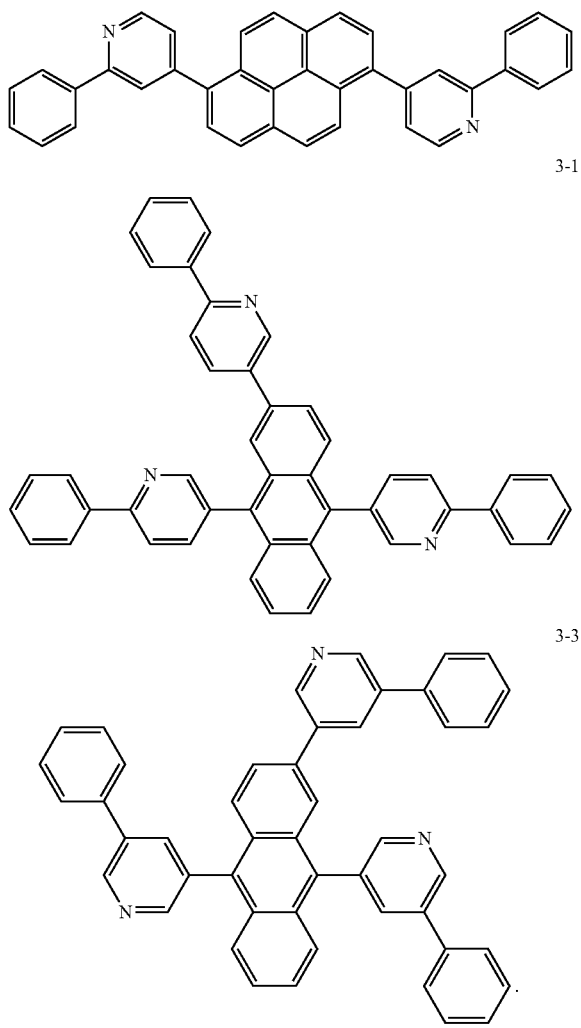

2-37

3-1

3-3

13. The organic electroluminescent apparatus of claim 9, wherein the organic luminescent medium comprising a luminescent layer and an electron transport functional layer, wherein the organic material of claim 1 is contained in the electron transport functional layer.

14. The organic electroluminescent apparatus of claim 13, wherein the electron transport functional layer further contains another electron transport material selected from the group consisting of oxazole compounds, metal chelates, triazole compounds, imidazole compounds, phenanthroline compounds or anthracene compounds.

15. The organic electroluminescent apparatus of claim 14, wherein the oxazole compounds, metal chelates, triazole compounds, imidazole compounds, phenanthroline compounds or anthracene compounds are selected from the group consisting of: 2-(4-tertbutylphenyl)-5-(4-biphenyl)-1,3,4-oxadiazole, tris(8-hydroxyquinolato)aluminum, 3-(4-biphenyl)-4-phenyl-5-(4-butylphenyl)-1,2,4-triazole, 4,7-diphenyl-1,10-phenanthroline, 2,9-dimethyl-4,7-diphenyl-1,10-phenanthroline, and 2-phenyl-9,10-dinaphthylanthracene.

16. The organic electroluminescent apparatus of claim 9, wherein the organic luminescent medium comprising a luminescent layer and an electron inject and transport functional layer, wherein the organic material of claim 1 is contained in the electron inject and transport functional layer, and the electron inject and transport functional layer further contains a dopant selected from the group consisting of alkaline metals, alkaline metal oxides, alkaline metal halides, alkaline metal nitrides, and alkaline metal salts.

17. The organic electroluminescent apparatus of claim 16, wherein the dopant is selected from the group consisting of lithium, cesium, lithium nitride, lithium fluoride, lithium cobaltate, lithium oxide, 8-hydroxyquinolato lithium, cesium carbonate, potassium borohydride, lithium borohydride, sodium fluoride, sodium chloride, cesium fluoride, cesium chloride, and rubidium oxide.

18. The organic electroluminescent apparatus of claim 16, wherein the electron inject and transport functional layer has a thickness of 2 nm to 40 nm, and a doping ratio of the dopant in the electron inject and transport functional layer is 0.1% to 49% by weight based on the organic material of claim 1.

19. The organic electroluminescent apparatus of claim 18, wherein the electron inject and transport functional layer has a thickness of 5nm to 25nm, and the doping ratio of the dopant in the electron inject and transport functional layer is 0.5% to 30% by weight based on the organic material of claim 1.

20. The organic electroluminescent apparatus of claim 16, wherein a buffer layer is further included between the electron inject and transport functional layer and the luminescent layer, and the material of the buffer layer is selected from the organic material as defined in claim 1, or selected from the group consisting of oxazole compounds, metal complexes, triazole compounds, imidazole compounds, quinoline compounds, oxaline compounds, phenazine compounds, and phenanthroline compounds.

21. The organic electroluminescent apparatus of claim 20, wherein the material of the buffer layer is selected from the compounds defined in claim 2.

22. The organic electroluminescent apparatus of claim 20, wherein the material of the buffer layer is selected from the group consisting of 2-(4-tertbutylphenyl)-5-(4-biphenyl)-1,3,4-oxadiazole, tris(8-hydroxyquinolato)aluminum, 3-(4-biphenyl)-4-phenyl-5-(4-butylphenyl)-1,2,4-triazole, 4,7-diphenyl-1,10-phenanthroline, 2,9-dimethyl-4,7-diphenyl-1,10-phenanthroline, 2-phenyl-9,10-dinaphthylanthracene, and an organic material having a chemical structure selected from:

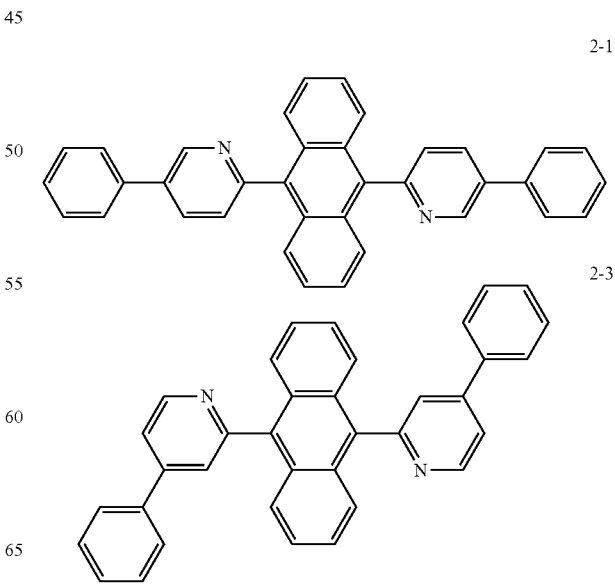

2-1

2-3

2-5
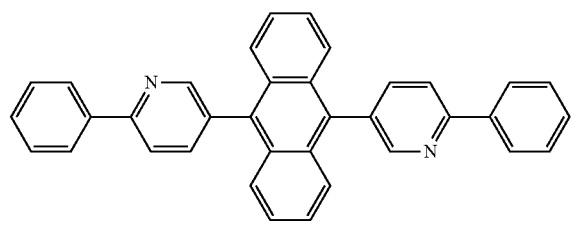
2-7
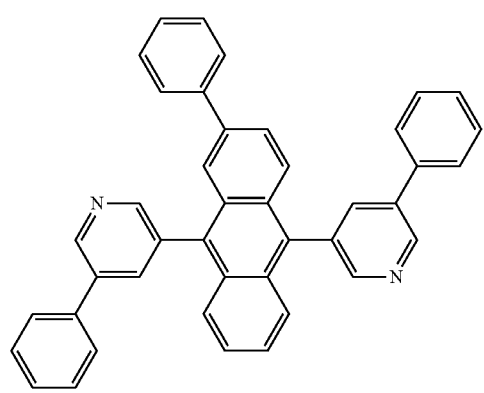
2-9
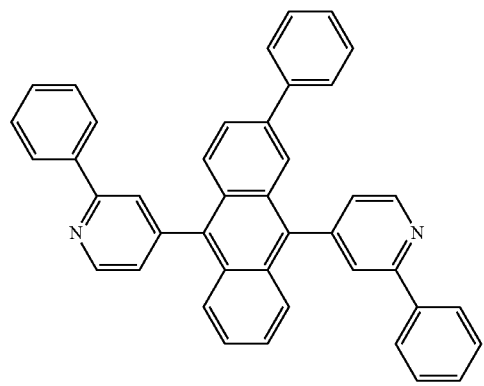
2-11
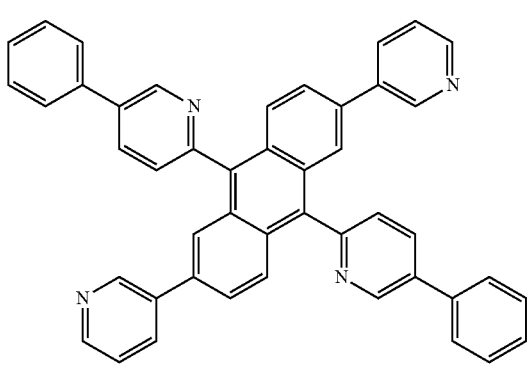
2-13
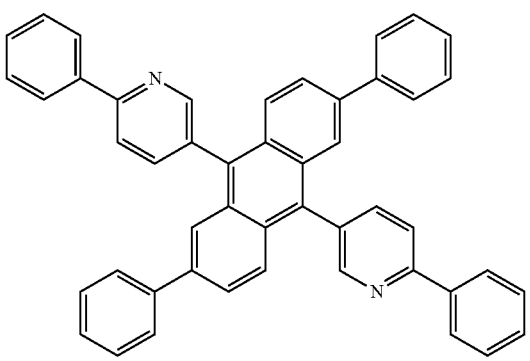
2-15
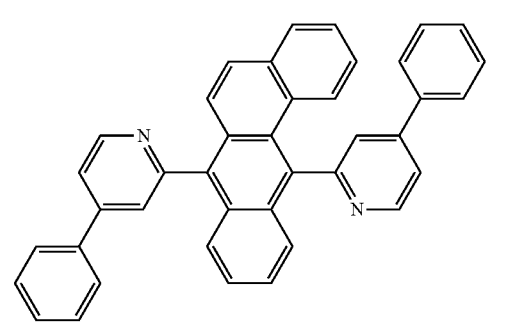
2-18
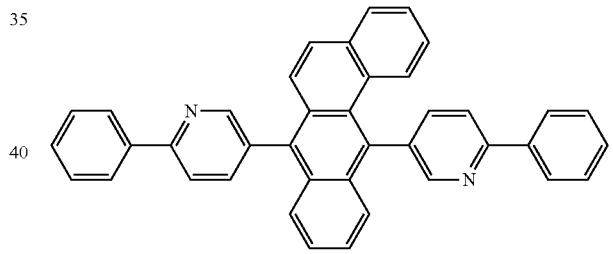
2-19
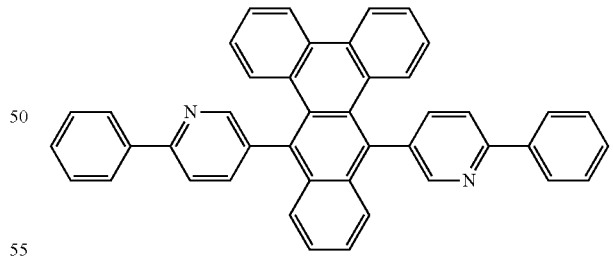
2-21
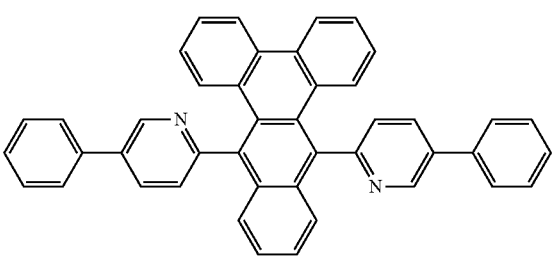

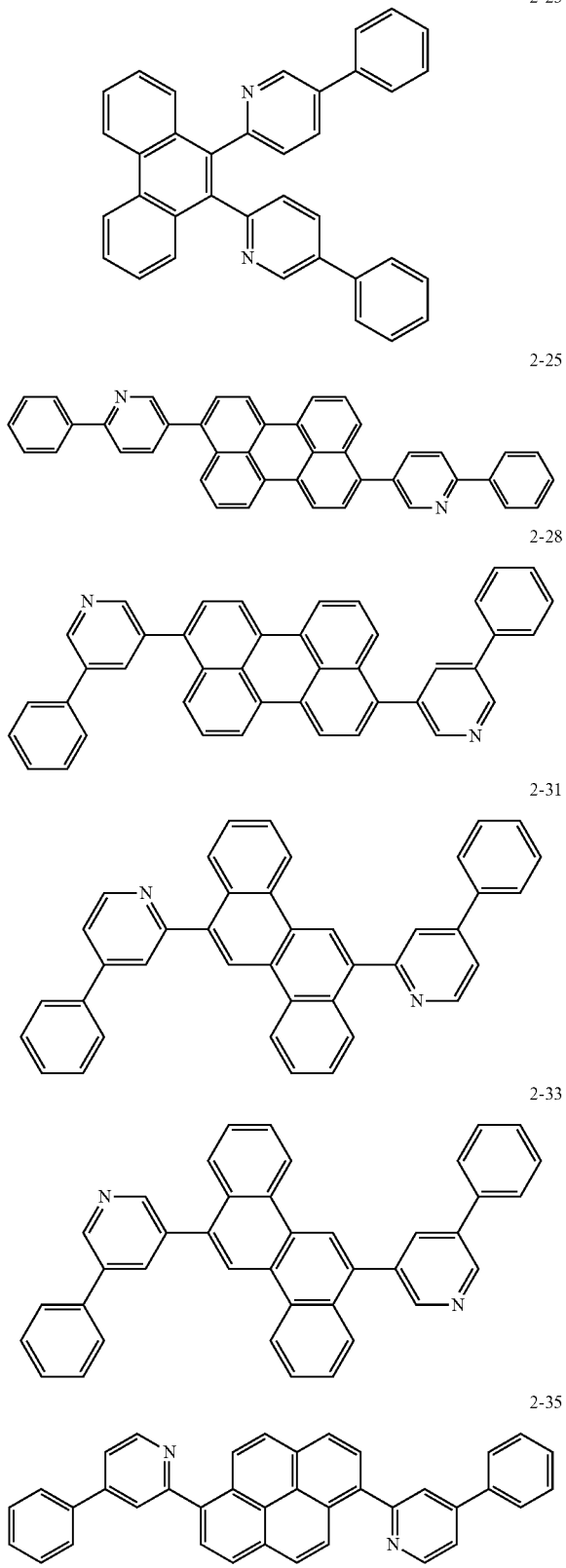

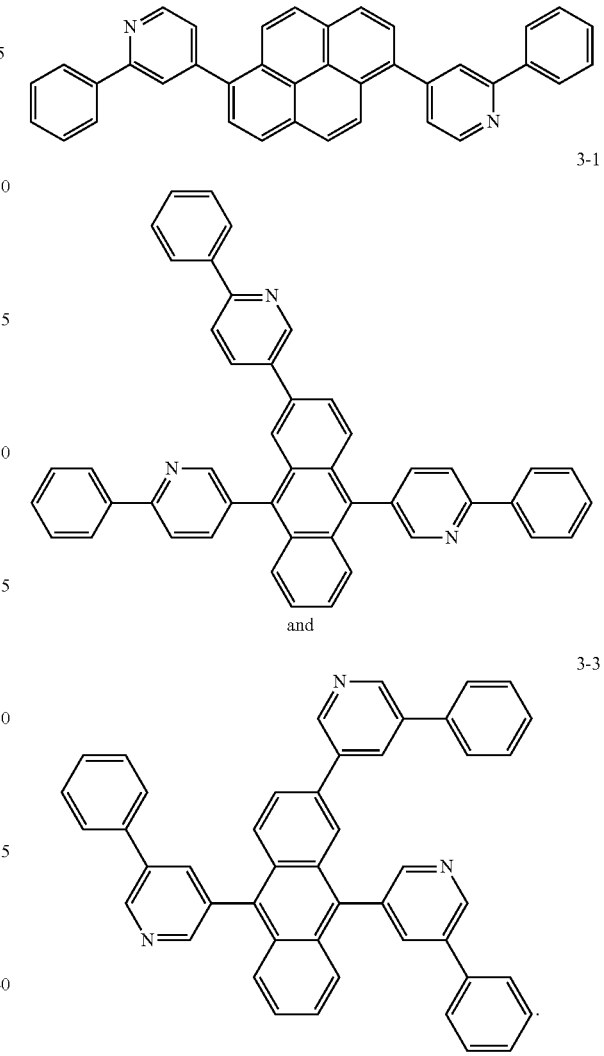

23. The organic electroluminescent apparatus of claim 20, wherein the buffer layer has a thickness of 2 nm to 20 nm.

24. The organic electroluminescent apparatus of claim 9, wherein the organic luminescent medium comprising at least two luminescent units, a connection layer being disposed between the luminescent units, wherein the organic material of claim 1 is contained in the connection layer.

25. The organic electroluminescent apparatus of claim 24, wherein a dopant selected from the group consisting of alkaline metals, alkaline metal oxides, alkaline metal halides, alkaline metal nitrides, and alkaline metal salts is further doped in the connection layer.

26. The organic electroluminescent apparatus of claim 25, wherein the dopant is selected from the group consisting of lithium, cesium, lithium nitride, lithium fluoride, lithium cobaltate, lithium oxide, 8-hydroxyquinolato lithium, cesium carbonate, potassium borohydride, lithium borohydride, sodium fluoride, sodium chloride, cesium fluoride, cesium chloride, and rubidium oxide.

* * * * *